United States Patent
Perron et al.

(10) Patent No.: US 7,700,294 B2
(45) Date of Patent: Apr. 20, 2010

(54) METHOD OF ISOLATING CYTOTOXIC HETEROCOMPLEX ASSOCIATED WITH MULTIPLE SCLEROSIS

(75) Inventors: Hervé Perron, Saint Genis les Olliéres (FR); Anne Eveno-Nobile, Dolomieu (FR); Jacques Portoukalian, Chuzelles (FR); Nicole Battail-Poirot, Lyons (FR)

(73) Assignees: Biomerieux, Marcy l'Etoile (FR); Institut National de la Sante et de la Recherche Medicale, Paris (FR)

( * ) Notice: Subject to any disclaimer, the term of this patent is extended or adjusted under 35 U.S.C. 154(b) by 385 days.

(21) Appl. No.: 10/582,674

(22) PCT Filed: Dec. 22, 2004

(86) PCT No.: PCT/FR2004/050748

§ 371 (c)(1),
(2), (4) Date: Jun. 12, 2006

(87) PCT Pub. No.: WO2005/063810

PCT Pub. Date: Jul. 14, 2005

(65) Prior Publication Data

US 2007/0065881 A1  Mar. 22, 2007

(30) Foreign Application Priority Data

Dec. 23, 2003 (FR) .................................. 03 15265

(51) Int. Cl.
*G01N 33/536* (2006.01)
*C07K 16/18* (2006.01)

(52) U.S. Cl. ..................... 435/7.1; 530/387.9
(58) Field of Classification Search ........................ None
See application file for complete search history.

(56) References Cited

U.S. PATENT DOCUMENTS 7,081,345 B1   7/2006  Roecklin et al.
7,510,843 B2 *  3/2009  Roecklin et al. ............. 435/7.1

FOREIGN PATENT DOCUMENTS

WO          01/05422   *  1/2001

OTHER PUBLICATIONS

Hornbeck 2000 (Current Protocols in Molecular Biology 11.2.1-11.2.22).*
Perron 2004 (6th International Symposium on Neurovirology and the HIV Neuroprotection Workshop, Sep. 10-14, 2004, published in Journal of Neurovirology 10 (Suppl. 3):p. 124).*
Presta, L., "Antibody engineering," *Current Opinion in Biotechnology* 3: 394-398 (1992).
Rieger, F. et al., "Un facteur gliotoxique et la sclérose en plaques—Gliotoxicity in multiple sclerosis," *C. R. Acad. Paris, Sciences de la vie/Life sciences 319*: 343-350 (1996).
Malcus-Vocanson, C. et al., "Glial toxicity in urine and multiple sclerosis," *Multiple Sclerosis 7*: 383-388 (2001).
Ménard, A. et al., "A gliotoxic factor and multiple sclerosis," *Journal of Neurological Sciences 154*: 209-221 (1998).
Malcus-Vocanson, C. et al., "A urinary marker for multiple sclerosis," *Lancet 351*: 1330 (May 1998).
Ménard, A. et al., "Gliotoxicity, reverse transcriptase activity and retroviral RNA in monocyte/macrophage culture supernatants from patients with multiple sclerosis," *FEBS Letters 413*: 477-485 (1997).
Ménard, A. et al., "Detection of a gliotoxic activity in the cerebrospinal fluid from multiple sclerosis patients," *Neuroscience Letters 245*: 49-52 (1998).
Benjelloun, N. et al., "DNA Fragmentation in Glial Cells in a Cerebral Biopsy from a Multiple Sclerosis Patient," *Cellular and Molecular Biology 44*(4): 579-583 (1998).
Blazar, B.R. et al., "Anti-CD3∈F(ab')$_2$ Fragments Inhibit T Cell Expansion in Vivo During Graft-Versus-Host Disease or the Primary Immune Response to Nominal Antigen," *Journal of Immunology 159*: 5821-5833 (1997).
Bird, R.E. et al., "Single-Chain Antigen-Binding Proteins," *Science 242*: 423-426 (Oct. 1988).
Arakawa, F. et al., "Cloning and Sequencing of the $V_H$ and $V_K$ Genes of an Anti-CD3 Monoclonal Antibody, and Construction of a Mouse/Human Chimeric Antibody," *Journal of Biochemistry 120*: 657-662 (1996).
Chaudhary, V.K. et al., "A recombinant immunotoxin consisting of two antibody variable domains fused to *Pseudomonas extotoxin*," *Nature 339*: 394-397 (Jun. 1989).
Jones, P.T. et al., "Replacing the complementarity—determining regions in a human antibody with those from a mouse," *Nature 321*: 522-525 (May 1986).
Riechmann, L. et al., "Reshaping human antibodies for therapy," *Nature 332*: 323-327 (Mar. 1988).
Galiana, E. et al., "Establishment of Permanent Astroglial Cell Lines, Able to Differentiate in Vitro, From Transgenic Mice Carrying the Polyoma Virus Large T Gene: An Alternative Approach to Brain Cell Immortalization," *Journal of Neuroscinece Research 26*: 269-277 (1990).

* cited by examiner

*Primary Examiner*—Daniel E. Kolker
(74) *Attorney, Agent, or Firm*—Oliff & Berridge, PLC (57) ABSTRACT

The invention relates to an isolated cytotoxic factor which is associated with multiple sclerosis and which is selected from the heterocomplex GM2AP/GM2/MRP14 and mutated GM2AP/GM2/MRP14, and to the method of detecting said factor in a biological sample to be tested. The inventive method comprises the following steps consisting in: (i) bringing the biological sample into contact with at least one capture antibody selected from antibodies that bind specifically to the GM2AP protein, to the mutated GM2AP protein, to the MRP14 protein, to the complex GM2AP/GM2, to the complex mutated GM2AP/GM2 and to the complex MRP14/GM2, and with at least one labeled detection antibody selected from antibodies that bind specifically to the GM2AP protein, to the mutated GM2AP protein, to the MRP14 protein, to the complex GM2AP/GM2, to the complex mutated GM2AP/GM2 and to the complex MRP14/GM2, and (ii) detecting and/or quantifying the cytotoxic factor by detecting and/or quantifying the labeled detection antibody.

16 Claims, 1 Drawing Sheet

METHOD OF ISOLATING CYTOTOXIC HETEROCOMPLEX ASSOCIATED WITH MULTIPLE SCLEROSIS

Multiple sclerosis is a chronic disease of the central nervous system in humans, which evolves through a succession of remission and exacerbation phases or according to a regular progression, and the anatomopathological characteristic of which consists of the formation of clearly delimited areas of demyelination in the white substance of the brain and of the spinal cord.

At the histological level, these areas exhibit, at the early stage of the lesional process, degradation of the peri-axonal myelin associated with damage to the glial cells responsible for this demyelination. An inflammatory macrophage activation involving microglial cells (resident tissue macrophages of the central nervous system), and also, probably, macrophages originating from infiltrated blood monocytes, is associated with this demyelination process and contributes to the destruction of the myelinated sheets. A relative depletion of glial cells is found at the center of the demyelinated area, whereas a proliferation of astrocytes develops at the periphery and can invade the demyelinated plaque to generate a fibrous or gliotic plaque. These sclerotic structures are the reason for the name given to the disease.

Another characteristic of these plaques is their virtually systematic association with a vascular element around which they develop.

At the histological level, a frequent impairment of the blood-brain barrier (BBB) consisting of the capillary endothelium is observed. One of the determining elements in the maintenance of the BBB consists of the underlying presence of cytoplasmic extensions of astrocytes, called astrocytic end-feet. The astrocytic end-feet probably induce the formation or allow the maintenance of tight junction structures which ensure the cohesion of the capillary endothelial barrier giving concrete expression to the BBB. Now, various pathological models refer to the impairment of the BBB and to a depletion of the astrocytic end-feet.

Moreover, in the lesional process of MS, the impairment of the BBB contributes to amplifying the associated inflammatory response, through the influx of lymphoid cells originating from the bloodstream. The contribution of the inflammation associated with the immune cells is considerable in MS and participates in the lesional process.

The etiology of MS is a source of current debate because the disease could have various causes. Hypotheses have been put forward regarding a bacterial and/or viral origin. Moreover, as described in patent application WO 95/21859, H. Perron et al. were led to search for one or more effecter agents of the pathogenic process resulting in the typical formation of demyelination plaques and in astrocytic gliosis. In the context of this study, they demonstrated the presence, in the cerebrospinal fluid (CSF) and the serum of MS patients, of at least one factor which exhibits toxic activity with respect to human or animal astrocyte or oligodendrocyte cells. This toxic activity is characterized by a cytomorphological disorganization of the network of intermediate filaments and/or a degradation of the proteins of said filaments and/or cell death by apoptosis of glial cells. They established a significant correlation between the in vitro detection of this toxic activity in CSF and serum samples from MS patients and multiple sclerosis, by means of a quantitative colorimetric assay with methyltetrazolium bromide (MTT) of living cells, as described in patent application WO 95/21859. Moreover, C. Malcus-Vocanson et al.[1,4] have shown that urine is a biological fluid very favorable for detecting the activity of this toxic factor and have developed a method using flow cytometry for detecting and/or quantifying adherent glial cells that are dead through apoptosis. All the information concerning this method is described in patent application WO 98/11439.

Assays were carried out using a protein fraction of CSF and of urine from MS patients in order to attempt to identify this toxic factor. The protein content of each fraction was separated on an SDS-PAGE 12% gel and observed after silver staining of the gel. Among the proteins observed, a protein fraction centered on an apparent molecular weight of approximately 21 kD was found as a minor component associated with the toxic activity detected in vitro and a fraction centered on an apparent molecular weight of approximately 17 kD was found as a predominant component associated with this toxic activity.

Injection of the fraction originating from CSF from MS patients, into the brain of Lewis rats, and post-mortem histological observation of brain sections from the rats made it possible to observe, three months after the injection, apoptosis of the astrocyte population and the formation of demyelination plaques. All the information is contained in patent application WO 97/33466. These observations are in accordance with those which could be made on brain sections from patients suffering from MS, after biopsy[5].

Proteins potentially associated with this toxic activity with respect to glial cells in biological samples from MS patients have been studied as described in patent application WO 01/05422. The proteins GM2AP (GM2 ganglioside activator precursor) and saposin B have thus been assayed in the urine of MS and non-MS patients. The results presented in patent application WO 01/05422 showed that GM2AP and saposin B were present at high concentrations in the urine of MS patients compared with the concentrations found in non-MS individuals, and that these two proteins which are codetected in the urine of MS patients could represent a marker for the pathology. The inventors had also established a correlation between the detection of the GM2AP and saposin B proteins in the urine and the gliotoxicity measured in this urine by means of the MTT assay and shown that a correlation existed between high urine concentration and gliotoxicity for these two proteins. The inventors concluded therefrom that the GM2AP and/or saposin B proteins were involved in the mechanism of gliotoxicity and that they could probably act in combination to induce gliotoxicity.

The present inventors have now wanted to determine the activity of the proteins identified in patent application WO 01/05422 using the MTT assay, and to see whether the gliotoxicity discovered in the urine of patients suffering from multiple sclerosis is related to the proteins identified.

Against all expectations, the present inventors have shown that it is neither the proteins identified in WO 01/05422 taken individually, nor the combination of the GM2AP/saposin B proteins which is involved in the gliotoxicity and that, entirely surprisingly, the agent responsible for the gliotoxic activity and involved in the cytotoxicity corresponds to a heterocomplex GM2AP/GM2/MRP14 (calgranulin B) or mutated GM2AP/GM2/MRP14, as described in the examples which follow. GM2 or ganglioside GM2 is a complex lipid present in cerebral tissue.

Thus, a subject of the present invention is the purified isolated cytotoxic factor, associated with multiple sclerosis, said cytotoxic factor being the heterocomplex GM2AP/GM2/MRP14 or mutated GM2AP/GM2/MRP14, it being understood that mutated GM2AP corresponds to the sequence SEQ ID No. 2. These purified isolated heterocomplexes are useful as markers for the MS pathology, and more specifically for a form of the disease, for a stage of the disease or for a period of activity of the disease, and also in the follow-up of patients treated for this pathology.

The present inventors have therefore developed a method, a composition and a reaction mixture for detecting and/or quantifying the heterocomplexes GM2AP/GM2/MRP14 and mutated GM2AP/GM2/MRP14 in samples from individuals liable to be suffering from multiple sclerosis or exhibiting clinical signs of this pathology.

The method consists in detecting and/or quantifying the cytotoxic factor, associated with multiple sclerosis, in a biological sample, by isolating the heterocomplex GM2AP/GM2/MRP14 or mutated GM2AP/GM2/MRP14 from said biological sample. The expression "isolating the heterocomplex" is intended to mean all the conditions which allow the specific detection of the heterocomplex. The isolation of said heterocomplex can be carried out by any appropriate means. By way of example, mention may be made of nondenaturing electrophoreses, column chromatographies, methods for degrading the compounds of the biological medium, with the exception of the heterocomplex (such as, for example, a treatment with proteinase K), and also any other method for detecting a physicochemical characteristic of said heterocomplex, such as the molecular mass or the isoelectric point, or any other appropriate means.

In one embodiment of the invention, use is made of at least one antibody or at least two antibodies that bind(s) specifically to the heterocomplex, and said cytotoxic factor is detected and/or quantified by demonstrating the formation of a complex consisting of the heterocomplex and the antibody or by demonstrating a complex consisting of the heterocomplex and the two antibodies. Preferably, at least one of said antibodies is a capture antibody and at least the other of the antibodies is a detection antibody.

The capture antibody is chosen from antibodies that bind specifically to the complex GM2AP/GM2, to the complex mutated GM2AP/GM2, to the complex MRP14/GM2, to the complex GM2AP/MRP14 and to the complex mutated GM2AP/MRP14, and the detection antibody is chosen from antibodies that bind specifically to the complex GM2AP/GM2, to the complex mutated GM2AP/GM2, to the complex MRP14/GM2, to the complex GM2AP/MRP14 and to the complex mutated GM2AP/MRP14.

In another embodiment, the heterocomplex is isolated by means of at least two antibodies, at least one of which binds specifically to GM2AP or mutated GM2AP of the heterocomplex, and at least the other of which binds specifically to MRP14 of the heterocomplex, and said cytotoxic factor is detected and/or quantified by demonstrating the formation of a complex consisting of the heterocomplex and the two antibodies. Preferably, at least one of said abovementioned antibodies is a capture antibody and at least the other said antibody is a detection antibody.

In the abovementioned embodiments, the demonstration of the formation of the complex consisting of the heterocomplex and at least one antibody or of the heterocomplex and at least two antibodies can be carried out by any appropriate means, for example by screening as a function of size using a sorting device, by screening as a function of molecular mass using a separation column or by direct or indirect labeling of at least one antibody or by any other appropriate means.

In one embodiment, the method consists in (i) providing a biological sample to be tested, (ii) bringing said biological sample into contact with at least one capture antibody, said capture antibody being chosen from antibodies that bind specifically to the GM2AP protein, to the mutated GM2AP protein, to the MRP14 protein, to the complex GM2AP/GM2, to the complex mutated GM2AP/GM2 and to the complex MRP14/GM2, and with at least one labeled detection antibody, said detection antibody being chosen from antibodies that bind specifically to the GM2AP protein, to the mutated GM2AP protein, to the MRP14 protein, to the complex GM2AP/GM2, to the complex mutated GM2AP/GM2 and to the complex MRP14/GM2, and (iii) detecting and/or quantifying the cytotoxic factor by detecting and/or quantifying the labeled detection antibody, it being understood that mutated GM2AP corresponds to the sequence SEQ ID No. 2.

Preferably, the detection and/or the quantification of the cytotoxic factor is (are) carried out using various immunoassay principles which are well known to those skilled in the art, such as ELISA and ELFA, and use is advantageously made of a "sandwich" immunoassay. The "sandwich"—immunoassay can be carried out in one or more steps, i.e. without a washing step or with one or more washing steps.

The detection antibody or antibodies is (are) labeled with any appropriate label. The labeling can thus be radioactive labeling, labeling with an enzyme, labeling with a fluorescent molecule, labeling with a vitamin, or colorimetric labeling. In the present invention, the label is preferably a vitamin, biotin, the detection is carried out by the addition of streptavidin coupled to horseradish peroxidase and the visualization is carried out by the addition of ortho-phenylenediamine dihydrochloride.

The capture antibody or antibodies is (are) directly or indirectly immobilized on a solid phase.

The term "antibody" used in the present invention encompasses monoclonal and polyclonal antibodies, fragments thereof and derivatives thereof. The term "antibody fragment" is intended to mean the F(ab)2, Fab, Fab' and sFv fragments of a native antibody[6,7], and the term "derivative" is intended to mean, inter alia, a chimeric derivative of a native antibody[8,9]. These antibody fragments and antibody derivatives conserve the ability to bind selectively to the target antigen. It may be advantageous to use humanized antibodies. "Humanized" forms of nonhuman, for example murine, antibodies are chimeric antibodies which comprise a minimum sequence derived from a nonhuman immunoglobulin. For the most part, humanized antibodies are human immunoglobulins (recipient antibody) in which residues of a hypervariable region of the recipient are replaced with residues of a hypervariable region of a nonhuman donor species (donor antibody), such as mouse, rat, rabbit or nonhuman primate, having the desired specificity, affinity and capacity. In certain cases, the residues (FR) of the Fv region of the human immunoglobulin are replaced with corresponding nonhuman residues. Furthermore, humanized antibodies can comprise residues which are not found in the recipient antibody or in the donor antibody. These modifications are made so as to improve the effectiveness of the antibody. In general, the humanized antibody will comprise at least and preferably two variable domains, in which all or virtually all of the hypervariable loops correspond to a nonhuman immunoglobulin and all or virtually all of the FR regions will be those of a human immunoglobulin. The humanized antibodies may optionally also comprise at least one part of a constant region (Fc) of an immunoglobulin, such as a human immunoglobulin[10,11,12]. Mention may in particular be made of the anti-GM2AP and anti-MRP14 antibodies described in application WO 01/05422.

However, the surprising discovery that the agent responsible for the gliotoxic activity and involved in the cytotoxicity corresponds to the heterocomplex GM2AP/GM2/MRP14 or mutated GM2AP/GM2/MRP14 allows the production of anti-heterocomplex antibodies that are capable of binding specifically to the complex GM2AP/GM2, to the complex mutated GM2AP/GM2, to the complex MRP14/GM2, to the complex GM2AP/MRP14 or to the complex mutated GM2AP/MRP14. The production of such antibodies is well known to those skilled in the art. The heterocomplex GM2AP/GM2/MRP14 or mutated GM2AP/GM2/MRP14 is used as an immunogen for immunizing BALB/c mice by intraperitoneal injection. The first injection is given with complete Freund's adjuvant. The other injections are given at intervals of 4-8 weeks, with incomplete Freund's adjuvant. A final booster is given a few days before the fusion in physiological saline. After this booster, the spleens of the immunized mice are removed and the splenocytes are collected. The fusion of the spleen cells with cells of a myeloma line is then carried out and the cells secreting antibodies which recognize, in ELISA, the heterocomplex used for the immunization are selected. Finally, the clones producing antibodies specific for the immune heterocomplex, i.e. that recognize neither GM2AP, nor mutated GM2AP, nor MRP14, alone, are selected.

The abovementioned antibodies can be used in the method for detecting and/or quantifying the cytotoxic factor, either alone or in combination.

In a preferred embodiment of the method of the invention, the test sample is subjected to a prior treatment comprising:
a step consisting in digesting the proteins of the sample with proteinase K; a step consisting in inactivating the proteinase K, for example by precipitation with trichloroacetic acid, and a step consisting in neutralizing the pH, for example by the addition of a tris-maleate buffer.

The biological test sample is serum, plasma, urine or cerebrospinal fluid, preferably urine.

Preferably, the antibodies used in the method of the invention are the following monoclonal and polyclonal antibodies: 10E11A11, 13D1E5, 13H9C9, 19C11C10, 2G12H5, 79, 2B9H2, 4A7B10, 5H7C10 and 196. However, it is quite obvious that any antibody that exhibits the characteristic of binding specifically to the GM2AP protein, to the mutated GM2AP protein, to the MRP14 protein, to the complex GM2AP/GM2, to the complex mutated GM2AP/GM2, to the complex MRP14/GM2, to the complex GM2AP/MRP14 or to the complex mutated GM2AP/MRP14 is part of the invention, the methods for obtaining such antibodies being well known to those skilled in the art, as described above.

Preferably, the antibodies used in the sandwich ELISA detection and/or quantification assay of the invention are the following monoclonal and polyclonal antibodies:
capture antibodies 10E11A11, 13D1E5, 2G12H5, 4A7B10, 5H7C10, 2B9H2, and 79;
detection antibodies 10E11A11, 4A7B10, 5H7C10, 2B9H2, 13H9C9, 19C11C10, 13D1E5 and 2G12H5.

The capture and detection antibodies are advantageously chosen from the pairs:
2B9H2/10E11A11,
10E11A11/4A7B10+5H7C10, 13D1E5+2G12H5/4A7B10+5H7C10, 79/4A7B10+5H7C10,
79/2B9H2,
4A7B10+5H7C10/10E11A11, 4A7B10+5H7C10/13H9C9+19C11C10, 2B9H2/100E11A11,
2B9H2/13H9C9+19C11C10, 13D1E5+2G12H5/4A7B10+5H7C10,
79/2B9H2,
4A7B10+5H7C10/10E11A11,
4A7B10+5H7C10/13D1E5+22G12H5,
2B9H2/13D1E5+22G12H5,
2B9H2/13H9C9+19C11C10.

The abovementioned monoclonal and polyclonal antibodies are novel and are also part of the subjects of the present invention. The method of producing them will be described in greater detail in the experimental section. The selected and preferred capture and detection antibody pairs are also novel and are also part of the subjects of the present invention.

A subject of the present invention is also a composition for detecting and/or quantifying the abovementioned cytotoxic (gliotoxic) factor in a biological-test sample, said composition comprising at least one antibody that binds specifically to the heterocomplex GM2AP/GM2/MRP14 or mutated GM2AP/GM2/MRP14. Preferably, said composition comprises at least two antibodies that bind specifically to the heterocomplex.

A subject of the present invention is also a composition for detecting and/or quantifying the abovementioned cytotoxic (gliotoxic) factor in a biological test sample, said composition comprising, in a reaction mixture and simultaneously, at least one capture antibody and at least one labeled detection antibody, said antibodies being chosen from the antibodies that bind specifically to the GM2AP protein, to the mutated GM2AP protein and to the MRP14 protein of the heterocomplex.

Preferably, the capture and detection antibodies are chosen from the following monoclonal and polyclonal antibodies: 10E11A11, 13D1E5, 13H9C9, 19C11C10, 2G12H5, 79, 2B9H2, 4A7B10, 5H7C10 and 196.

Advantageously, said composition comprises at least one capture antibody chosen from the antibodies 10E11A11, 13D1E5, 2G12H5, 4A7B10, 5H7C10, 2B9H2 and 79; and at least one detection antibody chosen from the detection antibodies 10E11A11, 4A7B10, 5H7C10, 2B9H2, 13H9C9, 19C11C10, 13D1E5 and 2G12H5.

The preferred compositions comprise the following capture and detection antibody pairs:
2B9H2/10E11A11,
10E11A11/4A7B10+5H7C10,
13D1E5+2G12H5/4A7B10+5H7C10,
79/4A7B10+5H7C10,
79/2B9H2,
4A7B10+5H7C10/10E11A11,
4A7B10+5H7C10/13H9C9+19C11C10,
2B9H2/10E11A11,
2B9H2/13H9C9+19C11C10,
13D1E5+2G12H5/4A7B10+5H7C10,
79/2B9H2,
4A7B10+5H7C10/10E11A11,
4A7B10+5H7C10/13D1E5+22G12H5,
2B9H2/13D1E5+22G12H5,
2B9H2/13H9C9+19C11C10.

A subject of the invention is also a reaction mixture for detecting and/or quantifying the abovementioned cytotoxic (gliotoxic) factor, said mixture comprising at least two antibodies, at least one of which binds specifically to GM2AP or mutated GM2AP of the heterocomplex, and at least the other of which binds specifically to MRP14 of the heterocomplex. The term "reaction mixture" is intended to mean a homogeneous or heterogeneous medium which simultaneously comprises at least the abovementioned two antibodies. Preferably, at least one of said antibodies is a capture antibody and at least the other of said antibodies is a detection antibody.

Another subject of the invention is a complex comprising the heterocomplex bound to at least two antibodies, at least one of the antibodies of which is specific for GM2AP or for mutated GM2AP, and at least the other antibody of which is specific for MRP14.

The sequence SEQ ID No. 1 corresponds to the sequence of the GM2AP protein.

The sequence SEQ ID No. 2 corresponds to the sequence of the GM2AP protein mutated in exon 2, at position 40 (replacement of an aspartic acid with a phenylalanine).

The sequence SEQ ID No. 3 corresponds to the sequence of the mutated GM2AP protein exhibiting mutations both in exon 1, in exon 2 and in exon 4.

In the detailed description which will follow, when reference is made to the GM2AP protein, the sequence to be taken into consideration is the sequence identified in the sequence identifier SEQ ID No. 1. Moreover, when reference is made to the mutated GM2AP protein, the sequence to be taken into consideration is the sequence identified in the sequence identifier SEQ ID No. 2; it being understood that, in the sequences SEQ ID No. 1 and SEQ ID No. 2, a valine or an alanine can be found without distinction at position 153, as explained in the experimental section in example 3. However, equivalent experiments can be carried out by taking into consideration the mutated GM2AP protein exhibiting mutations both in exon 1, in exon 2 and in exon 4, as identified in the sequence identifier SEQ ID No. 3.

FIGURE

The attached FIGURE represents the dose-response curve of the ternary complex GM2AP+MRP14+GM2 (GM2: 50 µg/ml final concentration). The amounts of MRP14 are represented along the x-axis (in ng) and the percentage cytotoxicity corresponding to the percentage of dead cells is represented along the y-axis. In the present FIGURE, the amounts of GM2AP in ng are, respectively, represented by the following symbols:

φ: 5 ng, π: 10 ng, ψ: 20 ng, υ: 50 ng and χ: 100 ng.

Figure 1:
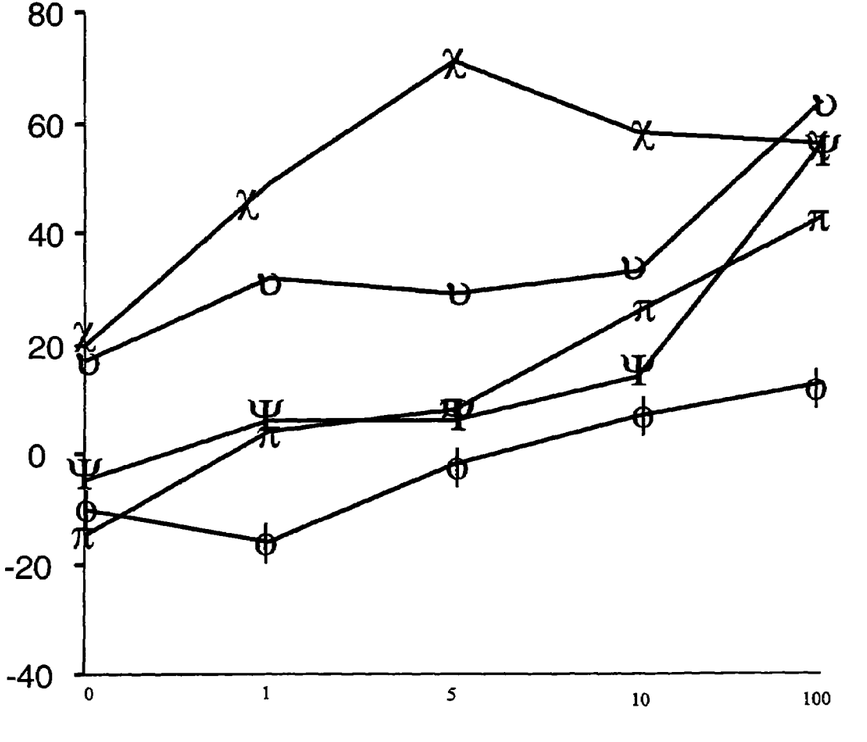

A similar experiment was carried out with the mutated GM2AP protein instead of the GM2 protein. The results obtained are similar to those given in the attached FIGURE.

EXAMPLES

Example 1

MTT Assay Protocol (i) "Coating" of the Plates with poly-L-lysine

250 µl of sterile poly-L-lysine solution (12.5 µg/ml) are deposited into all the wells of 48-well plates (Falcon 3078). After incubation for 2 hours at 37° C., the solution is removed by suction and replaced with 250 µl of sterile water so as to wash the wells. Once the wells have been emptied by suction, they are dried under the airstream of a microbiological safety station.

(ii) Cells Used

CLTT1-1 cells are astrocytes derived from transgenic mice expressing the large T gene of the polyoma virus[13]. These cells are cultured at 37° C. under a humid atmosphere at 5% $CO_2$, in Dubelcco's Modified Eagle's Medium (DMEM)/ Ham's F12 medium (50/50), 4.5 g/l of D-glucose, supplemented with 10% of nondecomplemented fetal calf serum (FCS), glutamax (580 mg/l), penicillin (500 units/i) and streptomycin (500 µg/l).

(iii) Cytotoxicity Assay

The test samples are prepared 24 hours before deposit for the toxicity assay and incubated at 4° C.

The 48-well plates "coated" with poly-L-lysine are seeded with CLTT 1-1 cells at a rate of 250 µl of cell suspension (6000 cells/ml) per well, i.e. 1500 cells/well.

After incubation for 24 hours at 37° C., in the humid atmosphere at 5% $CO_2$, the samples are deposited at the surface of the cell medium. Each sample is deposited in triplicate. Certain wells make it possible to evaluate cellular controls (C) (no deposit of sample) or "TUC" controls (deposit of 10 µl of TUC solution). The TUC reagent (20 mM Tris, 250 mM urea, 1 mM $CaCl_2$) is a solution that mimics the chemistry of the urine.

The deposit is homogenized and, in order to prevent any evaporation, a protective film is applied over the top of the plates.

After incubation for 72 hours at 37° C., in a humid atmosphere at 5% $CO_2$, the visualization by means of the MTT assay is carried out. The cell supernatant is removed by suction, taking care not to remove the cells from the bottom of the wells. 250 µl of MTT solution (0.5 mg/ml in culture medium) are deposited carefully onto the cells. After incubation for 3 hours at 37° C., the solution is removed by suction and the formazan crystals formed in the cells are solubilized with isopropanol, 1N HCl (40 µl/ml).

Once homogeneous, 70 µl of solution of each well of the 48-well plate are transferred into the wells of a 96-well plate, in order to carry out an optical density reading.

The absorbances are read at 570 nm/650 nm.

The percentage cytotoxicity can be calculated:

MeanC=mean of the absorbances of the controls
σC=standard deviation of the absorbances of the controls
CO=CutOff=MeanC=2 σC
OD=mean absorbance of the samples
% toxicity=(1−(OD/CO))×100

In order to be valid, the absorbances of each sample (in triplicate) must not have a standard deviation greater than 10% of the mean absorbance.

Example 2

Preparation of Pools of Urine 100 liters of MS urine (0.2-0.5 liter originating from the first morning micturition of patients) were collected. The urine from patients with a bacterial[4] contamination or that from patients treated with drugs liable to interfere with the gliotoxicity bioassay[4] were eliminated. The individual samples were tested for gliotoxicity and a final pool of 46 liters of urine with a significant gliotoxicity, by virtue of the MTT assay, was selected. In parallel, an equivalent volume of urine from normal donors with negative gliotoxicity, for each sample, was obtained. The steps consisting of concentration and purification of this material, the protein analysis and the identification strategy are presented below.

Purification of Proteins in the Urine

The MS positive and MS negative urine pools were purified so as to obtain a high concentration of proteins.

(i) Precipitation:
Precipitations with ammonium sulfate (Prolabo—ref. 21 333 365) were carried out on the MS positive and MS negative urine pools. The percentage of 60% saturated ammonium sulfate for 40% of urine, i.e. 390 grams of ammonium sulfate per liter of urine, was used. Each pool is dispensed, in fractions of 1.8 liters, into 2-liter bottles so as to improve the precipitation. The precipitation was carried out for 2×8 hours, at ambient temperature, with gentle stirring. After centrifugation of the urine pools at 3000 rpm for 10 min, at a temperature of 10° C., the pellet obtained is taken up in 20 mM Tris buffer containing 1 mM $CaCl_2$ and 0.25 M urea. The mixture was then centrifuged at 3000 rpm for 10 min. The supernatant contains the concentrated proteins. It is either used immediately for the following step, or frozen if the following step cannot be carried out continuously.

(ii) Ion Exchange Chromatography:

The solution containing the proteins was then passed over a DEAE Fast Flow gel (trade name, sold by Pharmacia). This step is carried out at low pressure on a Pharmacia column packed with gel. The buffers are introduced onto the column via a peristaltic pump which allows an even flow rate. The column-equilibrating buffer is 20 mM Tris buffer, pH 7. The fraction corresponding to the precipitation supernatant and containing a too high amount of salts is dialyzed against this buffer before being loaded onto the column. A salt-gradient elution makes it possible to recover the proteins. The elution gradient is effected by steps of 100, 200, 300 and 500 mM NaCl in the column-equilibrating buffer. The elution fractions are tested by means of the MTT assay. Only the positive fractions, i.e. the fractions eluted at 200 mM NaCl, are conserved. These fractions are treated immediately or conserved in the lyophilized state.

(iii) Purification:

A steric exclusion chromatography based on the difference in size and in shape of the proteins to be eluted was used. The fraction corresponding to the 200 mM NaCl elution is loaded onto the column. In the course of the elution, the low molecular weight proteins are retained and therefore eluted later than the large molecules. The purifications were carried out on HPLC with a TosoHaas TSK Prep G 3000 SW column, 21.5 mm in diameter and 300 mm in length. The molecular mass exclusion limit is 500 000 daltons. The elution buffer used contains 100 mM phosphate, 100 mM sodium sulfate, at pH 6.8. The separation of the mixture of proteins was carried out in 60 min. Only the fraction corresponding to a mass of 15-20 000 daltons was conserved. This fraction was dialyzed in a 20 mM Tris buffer containing 0.2 mM $CaCl_2$, pH 7.2, then lyophilized.

At each step, only the fractions exhibiting a significant toxic activity were retained for the subsequent step. A control for the toxic activity of the proteins was carried out at each step, using the MTT assay. Only the fractions exhibiting a significant toxic activity were retained for the additional purification step.

(iv) Additional Purification of the Proteins in the Urine by Reverse-Phase Chromatography:

The pools of urine originating from MS patients (MS positive pool) and from non-MS patients (MS negative pool), obtained after purification, were taken up in distilled water, and then diluted with a 0.2% TFA/10% acetonitrile solution so as to obtain a final concentration of approximately 130 to 140 µg/ml.

The separation by C8 reverse-phase HPLC was carried out on a Brownlee Aquapore column (trade name) sold by the company Perkin Elmer (column characteristics: 300 angstroms/7 µm/(100×4.6) mm). Two different columns were used respectively for the positive and negative pools. The injections were carried out by virtue of multi-injections of 250 µl. The proteins were eluted with a linear gradient of 5% to 15% of buffer A in 5 min, then of 15% to 100% of buffer B in 95 min, at a flow rate of 0.5 ml/min. The separation buffers A and B used are respectively the 0.1% TFA (Pierce No. 28904)/MilliQ water buffer and the 0.09% TFA/80% acetonitrile (Baker) buffer. The detection was carried out by measuring the UV absorbance at 205 and 280 nm. The fractions were collected as fractions of 1.5 ml and of 0.5-1 ml in the zone of interest. The fractions were frozen after collection, in dry ice.

The fractions collected were then dried in a Speed Vac and taken up in 100 µl of 0.1% TFA/30% acetonitrile. 20 µl of the fractions were transferred into 500 µl eppendorfs, dried and washed twice with 100 µl of MilliQ water, and then dried again.

The toxic activity of the proteins contained in each fraction collected after elution was determined using the MTT assay. Only the fraction X76/43 of the MS positive pool exhibits toxic activity in vitro. The number of this fraction corresponds to the order of the elution as a function of the elution conditions stated in the example. Its toxic activity was confirmed in vitro by FACS on murine astrocyte cells, as described in application WO 98/11439. Its profile on SDS-PAGE revealed protein bands at 55 kDa, 35 kDa, 20 kDa, 18 kDa, 14 kDa and 8 kDa. The corresponding fraction X76/43 of the MS negative pool, obtained from the control urine, did not exhibit any toxic activity by means of the MTT assay. Its profile on SDS-PAGE showed bands at 55 kDa, 35 kDa and 20 kDa.

Analysis of the Proteins Obtained by Separation on HPLC on SDS-TRICINE Gel

The protein content of the fraction X76/43 of the MS negative control pool and of the fraction X76/43 of the MS positive pool was observed after separation on SDS-TRICINE 16% gel and zinc/imidazole staining of the gel.

The fraction X76/43 collection pool obtained by HPLC was loaded onto a pre-poured SDS-TRICINE 16% gel with 10 wells and 1 mm thick (sold by the company Novex). The conditions for using the gel correspond to those recommended by the supplier. The sample is taken up in 75 µl of once concentrated sample buffer (SDS-TRICINE No. LC 1676, 1 ml twice concentrated+50 µl of β-mercaptoethanol (Pierce) diluted to ½ in water) and 25 µl of the sample are loaded onto the gel in triplicate. The fraction X76/43 collection pool originating from the MS negative pool was loaded onto the gel under the same conditions as those described for the MS positive pool. The migration on the two gels was carried out in parallel in the same migration tank (XCELL II NOVEX (trade name)) at a constant voltage of 125 mV for 2 hours. The tank was placed in a container containing ice. The gels were stained directly after migration by zinc/imidazole staining (staining kit 161-0440 sold by the company Biorad) so as to obtain a reversible negative staining.

Trypsin Digestion of the Gel Bands

All the protein bands visualized in the loadings of the fraction X76/43 were cut out and subjected to proteolysis in a trypsin solution overnight. The gel bands were cut into slices of 1 mm with a scalpel and transferred into eppendorf tubes. The eppendorfs were subjected to a centrifugation spike so as to bring down the gel pieces and, after centrifugation, 100 µl of washing buffer (100 mM $NH_4CO_3$/50% $CH_3CN$) were added to the gel pieces. After agitation for 30 min at ambient temperature, the supernatant was removed by 20 µl fractions and the washing step was repeated twice. The eppendorfs were dried for 5 min in a speed vac. 20 µg of trypsin (modified sequential grade PROMEGA V5111) (trade name) were taken up in 200 µl of digestion buffer (5 mM Tris, pH 8) and dissolved for 30 min at ambient temperature, with intermittent agitation, and 20 to 30 µl of resuspended trypsin were added to the gel pieces. The eppendorfs were centrifuged and stored in a warm room at 28° C. overnight. After digestion, the gel bands can be used immediately for the measurements of mass or frozen for subsequent use. Proteins of higher apparent molecular weights were found in the two fractions. On the other hand, the bands of apparent molecular weights 8, 14 and 18 kDa are visible only in the fraction X76/43 of the MS positive pool.

Example 3

Mass Spectrometry and Sequencing of the Proteins

Analysis by MALDI-TOF Mass Spectrometry of the Proteolytic Fragments

30 µl of extraction buffer (2% TFA/50% acetonitrile) are added to the samples. The eppendorfs to be analyzed are subjected to centrifugation for 5 min, and then to sonication for 5 min, and, finally, to centrifugation for 1 min.

14 deposits of 0.5 µl of matrix (α-cyano-4-hydroxy-trans-cinnamic acid at saturation in acetone) are made on a stainless steel disk. A thin uniform microcrystalline layer is obtained. 0.5 µl of a solution of 2% TFA/water is deposited onto this undercoat on the 14 deposits, and then 0.5 µl of sample to be analyzed is added. 0.5 µl of a saturated solution of α-cyano-4-hydroxy-trans-cinnamic acid in 50% acetonitrile/water is added to this drop thus formed. After drying at ambient temperature for 30 min, the crystalline deposits are washed with 2 µl of water, which are immediately removed with a blast of air. All the spectra are obtained on a BRUKER BIFLEX mass spectrometer (trade name) equipped with a reflectron. The measurements (90 to 120 firings of the laser over the entire deposit) are accumulated so as to obtain a mass spectrum which is the most representative of all the peptides present in the matrix-sample sandwich. For each deposit, a calibration with the trypsin autolysis peptides was carried out in order to be able to use a measuring accuracy of less than 100 ppm.

The mass spectrometry results were searched in the databanks using the MS-FIT algorithm of the Protein Prospector-software (http://prospector.ucsf.edu).

N-Terminal Sequencing of the Digestion Peptides (i) Extraction and Separation by HPLC of the Digestion Peptides The peptides obtained after digestion with trypsin were extracted in 3 times 30 min in a sonication bath with 0.1% TFA/60% acetonitrile. The extraction solutions were combined and dried to 20 µl in a speed vac. After dilution in 80 µl of buffer A (0.1% TFA/water), the extractions of the gel bands, digested with trypsin, were injected onto a C18/MZ-Vydac/(125×1.6) mm/5 µm column (trade name). The peptides were eluted at a flow rate of 150 µl/min and in a gradient ranging from 5% of buffer B (0.09% TFA/80% acetonitrile) to 40% of buffer B in 40 min, and then from 40% of buffer B to 100% of buffer B in 10 min. The detection was carried out by measuring the UV absorbance at 205 nm. The peaks were collected in 500 µl eppendorf tubes. The individual peptide peaks collected were then subjected to N-terminal amino acid sequence analysis.

(ii) N-Terminal Sequencing:

The fractions corresponding to a single mass peak were analyzed by Edman degradation on a sequencer (Perkin Elmer model 477A, Applied Biosystems). The sequencing conditions were those described by the constructor. A microcartridge was used for loading the samples and the PTH-amino acids were identified with an online HPLC system (Perkin Elmer model 120A, Applied Biosystems).

Results

The results of the analysis by mass spectrometry and of the sequencing are given in table 1 below.

TABLE 1

| MW (kDa) | IMS | | IS | |
|---|---|---|---|---|
| | MS | Control | MS | Control |
| 55 | Human serum albumin | Human serum albumin | ND | ND |
| 35 | Inter-alpha-trypsin inhibitor | Inter-alpha-trypsin inhibitor | ND | ND |
| 20 | Perlecan* | Perlecan* | Perlecan* | Perlecan |
| 20 | NI | NI | Retinol-binding protein | Retinol-binding protein |
| 20 | NI | NI | GM2-activating protein | Not present Not detected |
| 18 | GM2-activating protein | No band on the gel | GM2-activating protein | No band on the gel |
| 14 | MRP14 | No band on the gel | MRP14 | No band on the gel |
| 8 | Not identified | No band on the gel | Saposin B | No band on the gel |

MW: average molecular weight
IMS: identification by mass spectrometry
IS: identification by sequencing
NI: remaining peaks not identified
ND: not determined
*identical to the 20 kDa C-terminal fragment of perlecan probably resulting from prior proteolysis of the complete 467 kDa protein in the urine or during the purification process.

A mixture of co-purified proteins was also present both in the final MS purification fraction and in the corresponding control fraction. The proteins identified in these two samples were considered to be irrelevant due to the absence of gliotoxic activity in these two fractions.

Consequently, GM2AP (18 kDa), MRP14 or calgranulin B (14 kDa), and saposin B (10 kDa) were considered to be potential candidates for the gliotoxic activity.

Moreover, the N-terminal sequencing of the trypsin-digested fragments of the 18 kDa band in the MS fraction showed the presence of polymorphism in various positions of GM2AP; a mutation in exon 1, at position 19 of the GM2AP amino acid sequence, where an alanine is replaced with a threonine; a mutation in exon 2, where an aspartic acid is replaced with a phenylalanine at position 40 of the GM2AP amino acid sequence. This mutation has never been found in the genomic DNA of normal or affected donors; two other mutations in exon 2, respectively at positions 59 and 69 of the GM2AP amino acid sequence, which correspond to the replacement of an isoleucine with a valine and of a methionine with a valine. A mutation in exon 4, which consists of a replacement of a valine with an alanine at position 153 of the GM2AP amino acid sequence, was found to be a new polymorphism that had not been described, after various rounds of sequencing of the genomic DNA of lymphocytes originating from normal individuals (blood donors) and from patients suffering from multiple sclerosis. This mutation in exon 4 was found in 3 out of 27 MS patients tested, and also in 8 out of 27 control individuals, suggesting a normal polymorphism. Another mutation is found in exon 4, at position 171 of the GMPA2 amino acid sequence, where a lysine is replaced with a glutamine.

The amino acid sequences of GM2AP and of mutated GM2AP are respectively represented in the sequence identifier as SEQ ID No. 1 and SEQ ID No. 2, it being understood that, in these two sequences SEQ ID No. 1 and SEQ ID No. 2, a valine or an alanine can be found without distinction at position 153, since the mutation in exon 4 for this position suggests a normal polymorphism.

Example 4

Recombinant Proteins

Recombinant proteins (purchased or produced by transfection) were used to evaluate the gliotoxic potential of the candidate proteins.

The following "nonhuman" proteins, i.e. recombinant proteins produced in a prokaryotic expression system (*E. coli*) by transformation with a plasmid containing the insert to be expressed, or in a eukaryotic expression system in yeast or insect cells infected with the baculovirus having integrated the insert to be expressed, were used:

The MRP14 protein (or calgranulin B or S100A9) fused in the N-terminal position with a histidine tail and produced in *E. coli*; the MRP8 protein (or calgranulin A or S100A8) produced in *E. coli*; and the native human heterocomplex MRP14/MRP8 (or calprotectin), purchased from Dr C. Kerkhoff (University of Münster, Germany).

The GM2AP protein (ganglioside GM2-activating precursor) fused in the N-terminal position with a histidine tail produced in baculoviruses and the Sap B (saposin B) protein produced in yeast, purchased from Professor K. Sandhoff (Institut Kekule, University of Bonn, Germany).

These proteins have their own physiological activity described in the literature.

The "human" proteins, i.e. recombinant proteins produced in a eukaryotic expression system in human cells transfected with an appropriate plasmid having integrated the insert to be expressed, were produced according to the protocol described below.

293T cells (primary human embryonic kidney cells transformed with an adenovirus type 5, expressing the large T antigen) were cultured at 37° C. in a humid atmosphere at 5% $CO_2$, in DMEM, 4.5 g/l of D-glucose, supplemented with 10% of decomplemented fetal calf serum (FCS), glutamax (580 mg/l), penicillin (500 units/l) and streptomycin (550 μg/l).

To carry out the transient transfection, appropriate plasmids containing the cDNA of the proteins of interest, MRP14, GM2AP and mutated GM2AP (aspartic acid/phenylalanine/position 40) preceded by a secretion peptide (IgK) in the N-terminal position, were used.

The 293T cells were transfected with a "Transfectant" reagent composed of lipids which complex and transport the DNA into the cells. The 293T cells are trypsinized, seeded at 2 million cells per 75 $cm^2$ flask, and incubated overnight at 37° C. in a humid atmosphere at 5% $CO_2$ in 10 ml of culture medium (DMEM, 4.5 g/l of D-glucose, supplemented with 10% of decomplemented fetal calf serum (FCS), glutamax (580 mg/l), penicillin (100 units/ml) and streptomycin (100 μg/ml)).

The transfection solution is prepared extemporaneously using the ratio 3/2 [volume of Transfectant (μl)/amount of plasmid DNA (μg)], qs 1 ml of FCS-free medium.

After 45 minutes of contact at ambient temperature, the transfection solution is added dropwise to a nonconfluent cell layer.

After incubation for 72 hours at 37° C., in a humid atmosphere at 5% $CO_2$, the supernatants are recovered, and centrifuged for 10 minutes at 2500 rpm.

The quantification of protein produced is then carried out either with the MRP Enzyme Immunoassay kit (trade name) sold by BMA Biomedicals AG, Augst, Switzerland, according to the information sheet for the human recombinant MRP14 protein, or by the semi-quantitative Western blotting technique with anti-GM2AP rabbit polyclonal antibodies. These techniques give indicative values for a relative comparison.

The crude supernatants derived from this production will be used in particular for the toxic activity and detection assays.

Example 5

Toxicity of the "Nonhuman" Proteins

The toxicity of the "nonhuman" recombinant proteins MRP14, MRP8, GM2AP and SapB was evaluated by means of the MTT assay.

The proteins were tested in a range defined from the evaluation of the concentration of each protein in various urines. The ranges are prepared in various buffers, either in the TUC solution, or in two types of urine: urine originating from patients suffering from multiple sclerosis and which was toxic with the MTT assay (MS urine), and urine originating from a recruitment of non-MS donors, which was not toxic with the MTT assay (normal urine). The urine was treated beforehand for 30 min at 56° C. and filtered.

The results show that, taken individually, the proteins tested in the TUC solution and in the normal urine are not toxic with the MTT assay. No significant effect of the GM2AP, MRP14 and saposin B proteins is demonstrated in the MS urine with the MTT assay. An inhibition of the toxicity is noted with an MRP8 dose greater than or equal to 3-ng.

These results are shown in table 2.

TABLE 2A

| | Range in the TUC solution | |
|---|---|---|
| Protein | Amount in ng | Cytotoxicity as % |
| GM2AP | 5 | −48 |
| | 2.5 | −19 |
| | 1.25 | −122 |
| | 0 | −55 |
| MRP14 | 10 | −20 |
| | 5 | −22 |
| | 2.5 | −34 |
| | 0 | −11 |
| Saposin B | 50 | −9 |
| | 40 | −8 |
| | 30 | −16 |
| | 20 | −3 |
| | 10 | −16 |
| | 0 | −18 |
| MRP8 | 3 | −18 |
| | 1.5 | −19 |
| | 0.5 | −14 |
| | 0 | −19 |

TABLE 2B

| | Range in the urine | | |
|---|---|---|---|
| Protein | Amount in ng | MS urine Cytotoxicity as % | Normal urine Cytotoxicity as % |
| GM2AP | 5 | 34 | −11 |
| | 2.5 | 41 | −7 |

TABLE 2B-continued

| | Range in the urine | | |
|---|---|---|---|
| Protein | Amount in ng | MS urine Cytotoxicity as % | Normal urine Cytotoxicity as % |
| | 1.25 | 32 | −13 |
| | 0 | 42 | −4 |
| MRP14 | 10 | 29 | −8 |
| | 5 | 29 | 10 |
| | 2.5 | 33 | 9 |
| | 0 | 37 | 7 |
| Saposin B | 100 | 44 | ND |
| | 80 | 54 | ND |
| | 50 | 58 | ND |
| | 30 | 67 | ND |
| | 20 | 70 | ND |
| | 10 | 69 | ND |
| | 0 | 62 | ND |
| MRP8 | 3 | −18* | 8 |
| | 1.5 | 50 | 5 |
| | 0.5 | 46 | 10 |
| | 0 | 40 | 8 |

For MRP14 and MRP8, the percentage cytotoxicity is a mean percentage cytotoxicity over 2 assays
ND: not determined
*In another MS urine, the same inhibition of toxicity is observed.

Combinations of GM2AP/MRP14, saposin B/MRP14 and saposin B/GM2AP/MRP14 proteins were then prepared in the TUC solution and in the two types of urine as described above. In "control" combinations, the heterocomplex MRP14/8 or the MRP8 protein replaced the MRP14 protein in the various GM2AP/MRP14/8, saposin B/GM2AP/MRP8 combinations. The "control" combinations were prepared in the same manner. All the combinations were incubated overnight at 4° C. before being tested for their toxicity using the MTT assay.

The results are given in table 3.

TABLE 3A

| Range in the TUC solution | | |
|---|---|---|
| Combinations of proteins | | % cytotoxicity |
| GM2AP (ng) | MRP14 (ng) | |
| 20 | 1 | −12 |
| 20 | 0.5 | −8 |
| 10 | 1 | −9 |
| 10 | 0.5 | 18* |
| 0 | 0 | 0 |
| GM2AP (ng) | MRP14/8 (ng) | |
| 20 | 20 | −14 |
| 20 | 10 | −21 |
| 10 | 20 | −12 |
| 10 | 10 | −16 |
| 0 | 0 | 0 |
| Sap. B (ng) | MRP14 (ng) | |
| 30 | 1 | −17 |
| 30 | 0.5 | −19 |
| 15 | 1 | −9 |
| 15 | 0.5 | −8 |
| 0 | 0 | 0 |
| GM2AP (ng) | MRP14 (ng) | Sap. B (ng) | |
| 20 | 1 | 30 | −11 |
| 20 | 1 | 15 | −4 |
| 20 | 0.5 | 30 | −15 |
| 20 | 0.5 | 15 | −14 |
| 10 | 1 | 30 | −9 |
| 10 | 1 | 15 | −5 |
| 10 | 0.5 | 30 | −21 |
| 10 | 0.5 | 15 | −17 |
| 0 | 0 | 0 | 0 |

MRP14/8: human native heterocomplex
Sap. B: saposin B
*mean of two assays

The results in table 3A show that the combinations GM2AP/MRP14, GM2AP/MRP14/8, saposin B/MRP14 and GM2AP/MRP14/saposin B have no toxic effect in the TUC, whatever the amount tested. Only the combination GM2AP (10 ng)/MRP14 (0.5 ng) appears to exhibit toxicity, but this toxic activity was not subsequently found in two additional comparable assays. Furthermore, additional assays were carried out with the combination GM2AP/MRP14 using various amounts of GM2AP and of MRP14. The results obtained confirmed that the combination GM2AP/MRP14 has no toxic effect in the TUC, whatever the amount tested.

TABLE 3B

| Range in the normal urine | | | | |
|---|---|---|---|---|
| Combination of proteins Amounts in ng | | | % cytotoxicity Normal urine 1 | % cytotoxicity Normal urine 2 |
| GM2AP | MRP14 | | | |
| 20 | 1 | | −10 | 26 |
| 20 | 0.5 | | 0 | 25 |
| 10 | 1 | | 3 | 8 |
| 10 | 0.5 | | −6 | 20 |
| 0 | 0 | | −19 | 10 |
| Sap. B | MRP14 | | | |
| 30 | 1 | | 0 | 16 |
| 30 | 0.5 | | −4 | 15 |
| 15 | 1 | | −10 | 13 |
| 15 | 0.5 | | 3 | 11 |
| 0 | 0 | | −19 | 10 |
| GM2AP | MRP14 | Sap. B | | |
| 20 | 1 | 30 | −19 | 19 |
| 20 | 1 | 15 | 8 | 9 |
| 20 | 0.5 | 30 | −27 | 25 |
| 20 | 0.5 | 15 | 16 | 13 |
| 10 | 1 | 30 | 7 | 17 |
| 10 | 1 | 15 | 5 | 32 |
| 10 | 0.5 | 30 | 14 | 23 |
| 10 | 0.5 | 15 | 4 | 22 |
| 0 | 0 | 0 | −88 | 12 |

Sap. B: saposin B

As emerges from table 3B, the combination GM2AP/MRP14 is toxic in the normal urine since the toxicity increases as a function of the increase in the amount of GM2AP protein. However, this toxicity appears to be relatively unstable and relatively unreproducible and seems to be dependent on the urine sample (see comparison of the percentage cytotoxicity between normal urine 1 and normal urine 2, in table 3B).

The combination saposin B/MRP14 is at the limit of significance in the normal urine.

The results obtained with the combination GM2AP/MRP14/saposin B are difficult to interpret.

The toxicity of the combinations of GM2AP/MRP14 and saposin B/MRP14 proteins was also tested with respect to normal urine and toxic urine derived from patients suffering from multiple sclerosis (MS urine).

The results are shown in table 3C.

TABLE 3C

Range in the non-MS urine and MS urine

| Combinations of proteins (ng) | | % cytotoxicity Normal urine 1 | % cytotoxicity Normal urine 2 | % cytotoxicity MS urine |
|---|---|---|---|---|
| GM2AP | MRP14 | | | |
| 20 | 1 | −10 | 26 | 7 |
| 20 | 0.5 | 0 | 25 | 12 |
| 10 | 1 | 3 | 8 | 8 |
| 10 | 0.5 | −6 | 20 | 9 |
| 0 | 0 | −19 | 10 | 22 |
| Sap. B | mrp14 | | | |
| 30 | 1 | 0 | 16 | 32 |
| 30 | 0.5 | −4 | 15 | 28 |
| 15 | 1 | −10 | 13 | 16 |
| 15 | 0.5 | 3 | 11 | 14 |
| 0 | 0 | −19 | 10 | 22 |

Sap. B: saposin B

The combination saposin B/MRP14 has no toxic effect in the normal urine and the MS urine, whatever the amount tested.

The combination GM2AP/MRP14 does not exhibit any toxic effect with respect to normal urine 1, but exhibits a toxic effect with respect to normal urine 2 (when GM2AP increases, the toxicity of the urine increases). An inverse effect with respect to the MS urine is, moreover, noted. When the amount of MRP14 increases, the toxicity of the urine decreases.

Example 6

Toxicity of the "Human" Proteins

The proteins GM2AP, GM2AP mutated in exon 2 and MRP14 produced as described in example 3 were tested for their toxicity by means of the MTT assay, using the culture supernatants from the 293T cells containing them.

The following combinations were also effected using the 293T cell culture supernatants: GM2AP/MRP14, mutated GM2AP/MRP14, GM2AP/MRP14/MRP8. The combinations prepared were subsequently incubated overnight at 4° C., and were then tested for their toxicity by means of the MTT assay.

The results are shown in table 4.

TABLE 4A

| GM2AP (ng) | MRP14 (ng) | % C Batch 1 Assay 1 | % C Batch 1 Assay 2 | % C Batch 2 Assay 1 | % C Batch 2 Assay 2 |
|---|---|---|---|---|---|
| 20 | 1 | 4 | 23 | 11 | 12 |
| 20 | 0.5 | 31 | 29 | 20 | 20 |
| 20 | 0 | −26 | −26 | 8 | 8 |
| 10 | 1 | −13 | −13 | 0 | 8 |

TABLE 4A-continued

| GM2AP (ng) | MRP14 (ng) | % C Batch 1 Assay 1 | % C Batch 1 Assay 2 | % C Batch 2 Assay 1 | % C Batch 2 Assay 2 |
|---|---|---|---|---|---|
| 10 | 0.5 | −14 | −11 | 6 | 24 |
| 10 | 0 | −25 | −25 | 0 | 0 |
| 0 | 1 | −24 | −24 | ND | ND |
| 0 | 0.5 | −8 | −8 | ND | ND |

% C: percentage cytotoxicity
ND: not determined
Approximate concentrations of proteins in the supernatants: MRP14 batches 1 and 2: 350 ng/ml; GM2AP batch 1: 300 ng/ml, batch 2: 200 ng/ml For certain values, indicated in bold characters, some GM2AP/MRP14 combinations are weakly cytotoxic (from 20 to 30% cytotoxicity) with an optimum for the combination GM2AP (20 ng)/MRP14 (0.5 ng).

MRP14 alone is not cytotoxic. GM2AP alone is not considered to be cytotoxic, even though a very weak toxicity is found in assays 1 and 2 carried out on batch 2. This is because the reproducibility cannot be perfect since it depends on the supernatant production batch.

TABLE 4B

| GM2AP (ng) | MRP14 (ng) | % C Batch 3 Assay 1 | % C Batch 3 Assay 2 |
|---|---|---|---|
| 100 | 100 | 29 | 41 |
| 100 | 50 | 36 | 17 |
| 100 | 10 | 10 | 8 |
| 100 | 5 | 31 | 1 |
| 100 | 1 | rejection | 9 |
| 100 | 0 | 18 | 2 |
| 50 | 100 | rejection | 28 |
| 50 | 50 | 31 | 16 |
| 50 | 10 | 21* | −4 |
| 50 | 5 | 11 | −6 |
| 50 | 1 | −14 | −7 |
| 50 | 0 | 2 | −3 |
| 20 | 100 | 12* | 13 |
| 20 | 50 | rejection | 22 |
| 20 | 10 | −13 | 4 |
| 20 | 5 | −30 | 4 |
| 20 | 1 | −22 | −4 |
| 20 | 0 | ND | ND |
| 10 | 100 | 29* | 18 |
| 10 | 50 | 15 | 6 |
| 10 | 10 | −2 | −16 |
| 10 | 5 | −22 | −7 |
| 10 | 1 | −21* | −17 |
| 10 | 0 | ND | ND |
| 5 | 100 | 22* | 32 |
| 5 | 50 | −9 | 9 |
| 5 | 10 | −11 | 1 |
| 5 | 5 | −29 | −6 |
| 5 | 1 | −18 | −4 |
| 5 | 0 | ND | ND |
| 0 | 100 | 31 | 33 |
| 0 | 50 | 41* | 22 |
| 0 | 10 | 4 | 11 |
| 0 | 5 | ND | ND |
| 0 | 1 | ND | ND |

% C: percentage cytotoxicity
ND: not determined
Approximate concentration of GM2AP and MRP14 in the supernatant: 2 µg/ml
Rejection: % cytotoxicity rejected since the standard deviation of the OD values of the samples is greater than 50
*standard deviation of the OD values of the samples between 16 and 11
No comment: standard deviation of the OD values of the samples less than 10.

The results show that the proteins alone, in the supernatants, are not toxic, except in a nonspecific manner at very high amounts (10.0 ng of MRP14). Only the combination GM2AP (100 ng)/MRP14 (100 ng) can be considered to exhibit a relative cytotoxicity.

IF the GM2AP protein is replaced with the mutated GM2AP protein in this combination, the same type of toxicity is obtained for certain mixtures, as shown below.

TABLE 4C

| Mutated GM2AP (ng) | MRP 14 (ng) | % C Batch 2 Assay 1 | % C Batch 2 Assay 2 | % C Batch 2 Assay 3 |
|---|---|---|---|---|
| 20 | 1 | 16 | 25 | 53 |
| 20 | 0.5 | 18* | 18 | 50 |
| 10 | 1 | 12 | 15* | 21 |
| 10 | 0.5 | 10 | 20 | 25* |
| 10 | 0 | −7 | 0 | −7 |
| 0 | 1 | −9 | 13 | −16 |

% C: percentage cytotoxicity
*standard deviation of the OD values of the samples between 14 and 11
No comment: standard deviation of the OD values of the samples less than 10
Approximate concentration of proteins in the supernatants: mutated GM2AP: 200 ng/ml; MRP14: 350 ng/ml.

For many values, indicated in bold characters, the combination mutated GM2AP/MRP14 is toxic. The mutated GM2AP protein alone has no cytotoxic effect. MRP14 alone is not considered to exhibit any cytotoxic activity.

The cytotoxicity of the combinations of supernatants containing the human recombinant proteins, GM2AP/MRP14 and mutated GM2AP/MRP14, is found to be in the same order of magnitude, with a greater stability, as a function of the protein production batch, than with the nonhuman recombinant proteins. However, this does not correspond to the stability, the reproducibility and the intensity of the gliotoxic activity found in the biological fluids of MS patients.

TABLE 4D

| GM2AP (ng) | MRP14/18 (ng) | % C Batch 1 Assay 1 | % C Batch 1 Assay 2 | % C Batch 2 Assay 1 |
|---|---|---|---|---|
| 20 | 20 | 17 | −13 | 16 |
| 20 | 10 | 6 | −2 | 23 |
| 20 | 0 | −26 | −26 | 8 |
| 10 | 20 | −14 | −16 | 1 |
| 10 | 10 | −15 | −24 | 12 |
| 10 | 0 | −25 | −25 | 0 |

% C: percentage cytotoxicity
Approximate concentration of proteins in the supernatants: GM2AP (batch 1): 300 ng/ml, GM2AP (batch 2): 200 ng/ml. Concentration of native MRP14/8: 1.3 mg/ml.

It emerges from the results in table 4D that GM2AP alone has no cytotoxic activity and that, for certain values, indicated in bold characters, the combination GM2AP/MRP8 has a cytotoxic effect. This cytotoxicity is dependent on the supernatant batch used.

TABLE 4E

| Mutated GM2AP (ng) | MRP14/8 (ng) | % C Batch 2 Assay 1 |
|---|---|---|
| 20 | 20 | 5 |
| 20 | 10 | 6 |
| 20 | 0 | 15 |
| 10 | 20 | −18 |

TABLE 4E-continued

| Mutated GM2AP (ng) | MRP14/8 (ng) | % C Batch 2 Assay 1 |
|---|---|---|
| 10 | 10 | 4 |
| 10 | 0 | −2 |

% C: percentage cytotoxicity
Approximate concentration of proteins in the supernatants: mutated GM2AP: 200 ng/ml. Concentration of native MRP14/8: 1.3 mg/ml.

It emerges from table 4E that the combination mutated GM2AP/MRP8 does not exhibit any cytotoxic activity.

These studies show that none of the proteins identified in the gliotoxic fraction purified from MS urine reproduced, alone, the gliotoxic activity sought and that the combinations of proteins produced in the form of "nonhuman" or "human" recombinants reproduce only weakly, and relatively unreproducibly (even though an improvement is noted with the "human" recombinants), the gliotoxic activity. The results obtained do not meet all the criteria that characterize the gliotoxic activity (high activity, stability, reproducibility, dose-response effect).

The results show that an essential component, which was not identified in the protein analysis, is lacking.

The inventors then found, surprisingly, that lipids, in particular complex lipids, are advantageous candidates in this context. To this effect, ganglioside GM1, ganglioside GM2 and sulfatide were tested. Among these lipids, ganglioside GM2 proved to be the only one which was probative, as shown in the following examples.

Example 7

Toxicity of the "Human" Recombinant Proteins in Combination with Ganglioside GM2

Ganglioside GM2 (provided by Professor J. Portoukalian (Lyon, France)) is added, at a final concentration of 50 µg/ml, to the combinations of "human" recombinant proteins already prepared, involving the MRP14, GM2AP and mutated GM2AP proteins.

The combinations GM2AP/MRP14 and mutated GM2AP/MRP14 were tested in a protein range: 0, 5, 10, 20, 50, 100 ng for the GM2AP and mutated GM2AP recombinant proteins and up to 200 ng for the MRP14 protein. These ranges were prepared in combination or not in combination with ganglioside GM2.

After mixing, the combinations are incubated overnight at 4° C., and their toxicity is then evaluated using the MTT assay.

The results obtained are described in table 5 and in the attached FIGURE.

TABLE 5A

Measurement of the gliotoxic activity of the "human" proteins combined and associated with ganglioside GM2 (50 µg/ml final concentration)

| GM2AP (ng) | MRP14 (ng) | % C with gGM2 Batch 3 |
|---|---|---|
| 100 | 100 | 56* |
| 100 | 10 | 58 |
| 100 | 5 | 71 |
| 100 | 1 | 49 |
| 100 | 0 | 20 |
| 50 | 100 | 64* |
| 50 | 10 | 33 |

TABLE 5A-continued

Measurement of the gliotoxic activity of the "human" proteins combined and associated with ganglioside GM2 (50 µg/ml final concentration)

| GM2AP (ng) | MRP14 (ng) | % C with gGM2 Batch 3 |
|---|---|---|
| 50 | 5 | 29 |
| 50 | 1 | 32* |
| 50 | 0 | 17 |
| 20 | 100 | 56 |
| 20 | 10 | 14 |
| 20 | 5 | 6 |
| 20 | 1 | 6 |
| 20 | 0 | −5 |
| 10 | 100 | 43 |
| 10 | 10 | 26 |
| 10 | 5 | 8 |
| 10 | 1 | 4 |
| 10 | 0 | −15 |
| 5 | 100 | 13 |
| 5 | 10 | 7 |
| 5 | 5 | −2 |
| 5 | 1 | −16 |
| 5 | 0 | −10 |
| 0 | 100 | 30 |
| 0 | 10 | −23 |
| 0 | 5 | −19 |
| 0 | 1 | −8 |
| 0 | 0 | 8 |

% C: percentage cytotoxicity
gGM2: ganglioside GM2
*standard deviation OD of the samples between 13 and 11
No comment: standard deviation OD of the samples less than 10
Approximate concentrations in the supernatants: GM2AP and MRP14: 2 µg/ml The combination GM2AP/MRP14 combined with a constant concentration of ganglioside exhibits a gliotoxic effect which increases in parallel with the amount of MRP14 protein. Furthermore, for increasing amounts of the GM2AP protein (20 and 10 ng), a typical dose-response effect increasing in steps is obtained. However, at the end points, when there is not enough GM2AP protein (5 ng), there is no toxicity. Conversely, if there is too much GM2AP protein (50 ng and 100 ng), there is saturation of the toxicity with a plateau around 60%. In fact, only the CLTT1-1 cells undergoing proliferation in the culture during exposure to the gliotoxic factor are sensitive. This explains why the gliotoxicity plateaus do not reach 100%.

TABLE 5B

Measurement of the gliotoxic activity of the combined "human" proteins, combined or not combined with the ganglioside GM2 (50 µg/ml final concentration)

| Mutated GM2AP (ng) | MRP14 (ng) | % C Batch 4 without gGM2 Assay 1 | % C Batch 4 without gGM2 Assay 2 | % C Batch 4 with gGM2 Assay 1 | % C Batch 4 with gGM2 Assay 2 |
|---|---|---|---|---|---|
| 100 | 200 | ND | 10 | ND | 32 |
| 100 | 100 | −15 | −8 | 40 | 55 |
| 100 | 50 | −5 | −18 | 37 | 7 |
| 100 | 10 | −8 | −33 | 32 | −19 |
| 100 | 5 | −15 | −33 | 20 | −9 |
| 100 | 1 | −5 | −26 | 31 | −14 |
| 100 | 0 | −11 | −44 | 11 | −61 |
| 50 | 200 | ND | 19 | ND | 25 |
| 50 | 100 | 3 | 5 | 30 | 4 |
| 50 | 50 | 2 | −1 | 18 | −21 |
| 50 | 10 | −10 | −23 | 17 | −28 |
| 50 | 5 | −9 | −15 | −2 | −21 |
| 50 | 1 | −23 | −11 | 12* | −18 |
| 50 | 0 | −7 | −40 | 9 | −57 |
| 20 | 200 | ND | 8 | ND | 5 |
| 20 | 100 | −7 | −3 | 32 | −13 |
| 20 | 50 | −18 | −16 | 34 | −15 |
| 20 | 10 | −18 | −19 | 19 | −8 |
| 20 | 5 | −23 | −8 | 17 | 13 |
| 20 | 1 | −12 | −12 | 16 | −20 |
| 20 | 0 | −4 | −26 | 1 | −33 |
| 10 | 200 | ND | −2 | ND | 33 |
| 10 | 100 | −10 | −9 | 24 | 8 |
| 10 | 50 | −12 | −19 | 2 | −8 |
| 10 | 10 | −17 | −16 | −6 | −34 |
| 10 | 5 | −14 | −13 | −4 | −11 |
| 10 | 1 | −30 | −37 | −20 | −12 |
| 10 | 0 | ND | ND | ND | ND |
| 5 | 200 | ND | −10 | ND | 26 |
| 5 | 100 | −5 | −1 | 39 | −17 |
| 5 | 50 | −8 | −3* | 32 | −18 |
| 5 | 10 | −14 | −7 | 12 | −25 |
| 5 | 5 | −27 | −11 | 16 | −29 |
| 5 | 1 | −26 | −15 | 15 | −39 |
| 5 | 0 | ND | ND | ND | ND |
| 0 | 200 | ND | 45 | ND | 72 |
| 0 | 100 | 16 | 12 | 32 | 21 |
| 0 | 50 | −14 | −8 | 24 | −6 |
| 0 | 10 | 0 | −5 | 8 | −6 |
| 0 | 5 | ND | ND | ND | ND |
| 0 | 1 | ND | ND | ND | ND |
| 0 | 0 | ND | ND | −21 | −21 |

% C: percentage cytotoxicity
gGM2: ganglioside GM2
*standard deviation OD of the samples between 13 and 11
No comment: standard deviation OD of the samples less than 10

Without ganglioside GM2, the combinations mutated GM2AP/MRP14 are not gliotoxic. An overall increase in the cytotoxicity of the mixture with ganglioside GM2 is observed compared with the combinations without ganglioside. The variability of the measurements is apparently greater with the use of the mutated GM2AP protein. Overall, the activity appears to be significant and reaches a maximum plateau (cf.: maximum reached on the pool of cells undergoing proliferation during the assay, as discussed above) for the highest concentrations, according to a dose-effect with two variables, mutated GM2AP and MRP14.

In order to determine whether the action of ganglioside GM2 is indeed specific for the toxicity of the combinations of human recombinant proteins GM2AP/MRP14 (5 ng of MRP14 and 50 ng or 100 ng of GM2AP), other lipids were tested in parallel: ganglioside GM1 and sulfatide. The concentration ranges used are 0, 10, 20, 30 and 50-µg/ml final concentration. Once the lipids have been added, the combinations are incubated overnight at 4° C., and their toxicity is then evaluated in the MTT assay. The results, shown in tables 5C and 5D, show that only the combinations with ganglioside GM2 for the combinations GM2AP/MRP14 at the doses 30 µg/ml and 50 µ/ml are toxic for the glial cells (respectively 27% and 30%). The other lipids show no toxicity with the protein combinations.

TABLE 5C

Influence of ganglioside GM2 in the gliotoxic activity of the combined "human" recombinant proteins GM2AP/MRP14

| GM2AP (ng) | MRP14 (ng) | Concentration of gGM2 (µg/ml) | % cytotoxicity |
|---|---|---|---|
| 100 | 5 | 0 | −14 |
| 100 | 5 | 5 | −1 |
| 100 | 5 | 10 | 4 |
| 100 | 5 | 20 | 15 |
| 100 | 5 | 30 | 28 |
| 100 | 5 | 50 | 34 |
| 50 | 5 | 0 | 10 |
| 50 | 5 | 5 | 12 |
| 50 | 5 | 10 | 21 |
| 50 | 5 | 20 | 24 |
| 50 | 5 | 30 | 25 |
| 50 | 5 | 50 | 37 |
| — | 5 | — | −26 |
| 100 | — | — | −5 |
| 50 | — | — | −10 |
| 100 | — | 0 | −29 |
| 100 | — | 5 | −91 |
| 100 | — | 10 | −11 |
| 100 | — | 20 | −18 |
| 100 | — | 30 | −12 |
| 100 | — | 50 | −9 |
| — | 5 | 0 | −25 |
| — | 5 | 30 | −29 |
| — | 5 | 50 | −51 |

For the 100 ng GM2AP assay, this is a mean of two assays.
gGM2: ganglioside GM2

TABLE 5D

Influence of ganglioside GM2 in the gliotoxic activity of the combined "human" recombinant proteins GM2AP/MRP14

| GM2AP (100 ng)/MRP14 (5 ng) | % cytotoxicity |
|---|---|
| Without lipid | −12 |
| With GM2 (10 µg/ml) | −4 |
| With GM2 (20 µg/ml) | 2 |
| With GM2 (30 µg/ml) | 17 |
| With GM2 (50 µg/ml) | 25 |
| With GM1 (10 µg/ml) | −12 |
| With GM1 (20 µg/ml) | −4 |
| With GM1 (30 µg/ml) | −1 |
| With GM1 (50 µg/ml) | 2 |
| With sulfatide (10 µg/ml) | −12 |
| With sulfatide (20 µg/ml) | −19 |
| With sulfatide (30 µg/ml) | −13 |
| With sulfatide (50 µg/ml) | 5 |
| GM2AP control (100 ng) | −19 |
| GM2AP control (50 ng) | −32 |
| MRP14 control (5 ng) | −18 |
| GM2 control | 3 |
| GM1 control | rejection |
| Sulfatide control | −21 |

The results of the study show that:

the activity is associated with a protein heterocomplex involving the GM2AP or mutated GM2AP and MRP14 proteins;

it is the addition of a lipid, such as ganglioside GM2, which made it possible to obtain levels of activity, a reproducibility and dose-response effects that were compatible with the reproduction of the gliotoxic activity sought;

the mutation found on the GM2AP protein is not essential to the determinism of the gliotoxin in vitro. However, in vivo, it may be determining if it is necessary for the process of bio-availability of the GM2AP protein (for example, in the extracellular medium of the central nervous system).

These elements therefore demonstrate that a heterocomplex MRP14/GM2AP or MRP14/mutated GM2AP, combined with ganglioside GM2, is the main, or even sole, vector of the gliotoxic activity.

Example 8

Development of an Immunoassay for the Gliotoxic Complex—Preparation of the Samples Before the ELISA Assay (i) Samples Tested The samples tested are:

firstly, the human recombinant proteins in combination (GM2AP+MRP14), with or without ganglioside GM2, possibly diluted in normal urine, in order to detect the active recombinant complex, secondly, normal urine and MS urine for direct detection in the urine.

The samples, once prepared, are incubated for 24 hours at 4° C. for the detection assay.

The "human" recombinant proteins are used in the form of crude production supernatants, recovered after the transient transfection of 293T cells, with the appropriate negative controls in parallel. The systems used for assaying the MRP14 and GM2AP proteins are semi-quantitative and the amounts specified are indicative. The results are given in the examples which follow.

(ii) Treatment of the Samples

As is shown, in the following examples, the method of detection using the anti-MRP14 and anti-GM2AP antibodies in a "sandwich" ELISA format makes it possible to obtain positive results.

However, the inventors optimized this method of detection by carrying out a prior treatment of the sample, comprising a step consisting in digesting the proteins in the presence of proteinase K, followed by a step consisting in inactivating this protease by means of an original method of precipitation with trichloroacetic acid, and then neutralizing the pH with a tris-maleate buffer, selected for its subsequent compatibility with a sandwich ELISA assay.

This treatment of the sample, which is original in its various steps, was subsequently applied to the analyses which are presented in the following examples, and is described in detail below.

The samples (mixture of recombinant proteins or urine) are treated with proteinase K before detection of the complex according to the following protocol:

0.3 mg of proteinase K is added per 100 µl of sample. After digestion for one hour at 37° C., a precipitation with trichloroacetic acid is carried out, in order to inhibit the action of the proteinase K. 90% trichloroacetic acid (90 g of trichloroacetic acid per 48 ml of distilled water) is added to the sample (15% of the initial volume of the sample). The mixture is incubated for 30 minutes at 4° C.

After centrifugation for 30 minutes at 13 000 rpm, the pellet is taken up with a volume equal to the initial volume of the sample, with 0.2 M Tris maleate buffer, pH 6.2 (in the assays with no concentration factor) or any minimum volume (to carry out a concentration of the nondigested proteins in terms of volume).

After verification of the proteinase K-treated samples by means of the Western blotting technique, an observation can be made and the treatment can be optimized by increasing the amount of proteinase K and the action time thereof.

Example 9

Protocol for Detecting the Heterocomplex in a Sandwich ELISA Assay (i) Production of Antibodies: the Following Antibodies were Produced According to the Protocols Described Below:
polyclonal antibodies (bioMérieux):
rabbit polyclonal antibody 196 (anti-MRP14 peptide)
rabbit polyclonal antibody 79 (anti-recombinant GM2AP protein)
monoclonal antibodies (bioMérieux):
4A7B10
5H7C10
2B9H2
10E11A11
13H9C9
19C11C10
13D1E5
2G12H5.

Anti-GM2AP monoclonal antibodies: 10E11A11, 13D1E5, 13H9C9, 19C11C10 and 2G12H5.

The mice were immunized according to the following protocol: on day D0, intraperitoneal injection of 75 µg of the complex GM2AP-MRP14 in the presence of complete Freund's adjuvant. On days D23 and D37, a further intraperitoneal injection of the same amount of complex GM2AP-MRP14 in the presence of incomplete Freund's adjuvant. Four days before the fusion, give an intravenous injection of 50 µg of GM2AP antigen diluted in physiological saline.

1900 supernatants were screened by the indirect ELISA technique. The plates were "coated" with 100 µl of antigen (the complex GM2AP-MRP14) at 1 µg/ml in 0.05 M bicarbonate buffer, pH 9.6. The "coated" plates were incubated overnight at the temperature of 18-22° C. The plates were saturated with 200 µl of PBS-1% milk and subjected to incubation for 1 hour at 37°+/−2° C. 100 µl of supernatants or of ascites fluid in PBS buffer-0.05% tween 20 were added and the plates were incubated for 1 hour at 37°+/−2° C. 100 µl of goat anti-mouse Ig (H+L) polyclonal antibody conjugated to alkaline phosphatase (Jackson Immunoresearch ref: 115-055-062), diluted to 1/2000 in PBS buffer-1% BSA, were added and the plates were then incubated for 1 hour at 37°+/−2° C. 100 µl of PNPP (Biomérieux ref 60002990) at the concentration of 2 mg/ml in DEA-HCl (Biomérieux ref 60002989), pH=9.8, were added. The plates were subjected to incubation for 30 minutes at 37°+/−2° C. The reaction was blocked by adding 100 µl of 1N NaOH. Three washes were carried out between each step, with 300 µl of PBS-0.05% tween 20. An additional wash in distilled water was carried out before adding the PNPP.

150 supernatants were found to be positive by indirect ELISA with an OD>0.9. After the specificity assays, the abovementioned five antibodies are produced.

Anti-MRP14 monoclonal antibodies: 2B9H2, 4A7B10 and 5H7C10.

The mice were immunized according to the following protocol: on day D0, an intraperitoneal injection of 75 µg of the complex GM2AP-MRP14 in the presence of complete Freund's adjuvant. On days D23 and D37, intraperitoneal injection of the same amount of complex in the presence of incomplete Freund's adjuvant. Four days before the fusion, an intravenous injection of 50 µg of MRP14 antigen diluted in physiological saline.

1100 supernatants were tested and screened by the indirect ELISA technique, as described above. 300 supernatants were found to be positive with an OD>1. After the specificity assays, the abovementioned three antibodies were produced.

Rabbit polyclonal antibody 79 (anti-recombinant GM2AP protein).

The rabbits were immunized according to the following protocol: on day D0, the 1st blood sample of 10 ml was taken, and 75 µg of GM2AP were injected intraperitoneally in the presence of complete Freund's adjuvant (CFA) (75 µg of immunogen+qs 0.5 ml of 9‰ physiological saline+0.5 ml CFA). On days D28 and D56, the same amount of immunogen was injected intraperitoneally under the same conditions, in the presence of 0.5 ml of incomplete Freund's adjuvant (IFA). On day D63, a 2nd blood sample of 30 ml was taken from the ear without anticoagulant. A 3rd blood sample was taken under the same conditions on day D70.

Rabbit polyclonal antibody 196 (anti-MRP14 peptide).

The rabbits were immunized according to the following protocol:

The rabbits were immunized according to the following protocol: on day D0, the 1st blood sample of 10 ml was taken, and 80 µg of immunogen were injected intraperitoneally in the presence of complete Freund's adjuvant (CFA) (80 µg of immunogen+qs 0.5 ml of 9‰ physiological saline+0.5 ml CFA). On days D28 and D56, the same amount of immunogen was injected intraperitoneally under the same conditions, in the presence of 0.5 ml of incomplete Freund's adjuvant (IFA). On day D63, a 2nd blood sample of 30 ml was taken from the ear without anticoagulant. A 3rd blood sample was taken under the same conditions on day D70.

These antibodies are used for capture or for detection. When they are used for detection in the sandwich ELISA assay, the antibodies are biotinylated.

(ii) Sandwich ELISA Assay:

The treatment of the samples (proteinase K and TCA precipitation), if it takes place, is carried out after overnight incubation at 4° C. and before the sandwich ELISA detection assay.

The capture antibody is "coated" at 1 µg in carbonate-bicarbonate buffer (50 mM), pH 9.5; 100 µl are deposited in the wells of a 96-well microplate. The plate is covered with a protective film and incubated overnight at ambient temperature. After 3 washes in PBS (Phosphate Buffered Saline)-0.05% Tween, the nonspecific sites are blocked with PBS-0.05% Tween, goat serum-(1/10) for the monoclonal antibodies or 100 µl of casein hydrolyzate for the polyclonal antibodies. After 3 washes in PBS-0.05% Tween, the treated or nontreated samples are deposited at a rate of 100 µl per well and thus incubated for 1 hour 30 minutes at 37° C. with agitation.

After 3 washes in PBS-0.05% Tween, 100 µl of biotinylated detection antibodies at 1 µg/ml are deposited into each well and incubated for 1 hour 30 minutes at 37° C.

After 3 washes in PBS-0.05% Tween, 100 µl of streptavidin coupled to HRP (horseradish peroxidase) at 0.2 µg/ml are deposited into each well and incubated for 1 hour 30 minutes at 37° C. in order to amplify the signal.

After 3 washes in PBS-0.05% Tween, 100 µl of OPD (ortho-phenylenediamine dihydrochloride) solution at 2 g/l are deposited into each well and incubated for 10 minutes at ambient temperature. The reaction is stopped with 100 µl of 1N $H_2SO_4$. The optical density is read at 492 nm.

Similarly, for the production of anti-heterocomplex antibodies, the heterocomplex GM2AP/GM2/MRP14 or mutated GM2AP/GM2/MRP14 is used as immunogen for immunizing BALB/c mice by intraperitoneal injection. The first injection is given with complete Freund's adjuvant. The other injections are given at intervals of 4-8 weeks, with incomplete Freund's adjuvant. A final booster is given a few days before the fusion in physiological saline. After this booster, the spleens of the immunized mice are removed and the splenocytes are collected. The spleen cells are then fused with cells of a myeloma line and the cells secreting antibodies which recognize, by ELISA, the heterocomplex used for the immunization are selected. Finally, the clones producing antibodies specific for the immune heterocomplex, i.e. which recognize neither GM2AP, nor mutated GM2AP nor MRP14, alone, are selected.

Example 10

Detection of the Human Recombinant Heterocomplex

The enzymatic immunoassays for the gliotoxic activity characterized molecularly in the previous examples involve an antigen/antibody system using only the proteins involved (GM2AP, mutated GM2AP and MRP14 proteins), and antibodies (alone or in combination) capable of detecting this molecular complex.

The recombinant complex corresponds to the combination of the supernatants of recombinant proteins GM2AP (1000 ng) and MRP14 (50 ng), combined with a final concentration of 50 µg/ml of ganglioside GM2.

(i) Detection of the Recombinant Gliotoxic Heterocomplex Without Proteinase K Treatment In order to determine whether the toxic combinations were directly detectable, the "human" recombinant proteins MRP14 and GM2AP are combined with ganglioside GM2, incubated overnight at 4° C. and tested by means of the sandwich ELISA assay using the anti-MRP14 and anti-GM2AP antibodies.

The combinations [MRP14, GM2AP and ganglioside GM2] are diluted in normal urine (not gliotoxic in the MTT toxicity assay). The results are shown in table 6. These results show that anti-GM2AP capture antibody/anti-MRP14 detection antibody pairs recognize the recombinant complex in an extremely reproducible manner. The results are shown in table 6.

TABLE 6

| Capture antibody | Detection antibody | Positive assays | Assay total |
|---|---|---|---|
| 4A7B10 + 5H7C10 | 10E11A11 | 0 | 3 |
| | 13D1E5 + 2G12H5 | 0 | 1 |
| | 13H9C9 + 19C11C10 | 0 | 3 |
| | 79 | 0 | 1 |
| 2B9H2 | 10E11A11 | 1 | 3 |
| | 13D1E5 + 2G12H5 | 0 | 1 |
| | 13H9C9 + 19C11C10 | 0 | 3 |
| | 79 | 0 | 2 |
| 10E11A11 | 4A7B10 + 5H7C10 | 2 | 1 |
| | 2B9H2 | 0 | 2 |
| | 196 | 0 | 1 |
| 13D1E5 + 2G12H5 | 4A7B10 + 5H7C10 | 1 | 2 |
| | 2B9H2 | 0 | 2 |
| | 196 | 0 | 2 |
| 13H9C9 + 19C11C10 | 4A7B10 + 5H7C10 | 0 | 1 |
| | 2B9H2 | 0 | 1 |
| | 196 | 0 | 1 |

TABLE 6-continued

| Capture antibody | Detection antibody | Positive assays | Assay total |
|---|---|---|---|
| 79 | 4A7B10 + 5H7C10 | 2 | 2 |
| | 2B9H2 | 2 | 2 |
| | 196 | 0 | 1 |

Positive assays: number of positive assays
Assay total: total number of assays (ii) Detection of the Recombinant Gliotoxic Heterocomplex After Proteinase K Treatment As described above, the gliotoxic activity withstands proteinase K. Thus, by treating the samples (combination GM2AP+MRP14+GM2) with proteinase K, the noncomplexed proteins are destroyed, and the background noise is decreased.

As in the previous section, the combinations are incubated overnight at 4° C. However, before testing them, the samples are treated with proteinase K and precipitated with TCA (trichloroacetic acid), according to the protocol described in example 8 (ii).

The results are shown in table 7. These results show in particular that the anti-MRP14 capture antibody/anti-GM2AP detection antibody pairs [4A7B10+5H7C10]/[13H9C9+19C11C10], [4A7B10+5H7C10]/10E11A11, 2B9H2/10E11A11 and 2B9H2/[13H9C9+19C11C10] detect the recombinant complex in the supernatants diluted in the urine, after proteinase K treatment, in an extremely reproducible manner. The background noise is significantly reduced.

TABLE 7

| Capture antibody | Detection antibody | Positive assays | Assay total |
|---|---|---|---|
| 4A7B10 + 5H7C10 | 10E11A11 | 2 | 3 |
| | 13D1E5 + 2G12H5 | 0 | 1 |
| | 13H9C9 + 19C11C10 | 2 | 3 |
| | 79 | 0 | 1 |
| 2B9H2 | 10E11A11 | 2 | 3 |
| | 13D1E5 + 2G12H5 | 0 | 1 |
| | 13H9C9 + 19C11C10 | 2 | 3 |
| | 79 | 0 | 2 |
| 10E11A11 | 4A7B10 + 5H7C10 | 0 | 2 |
| | 2B9H2 | 0 | 1 |
| | 196 | 0 | 1 |
| 13D1E5 + 2G12H5 | 4A7B10 + 5H7C10 | 1 | 2 |
| | 2B9H2 | 0 | 2 |
| | 196 | 0 | 2 |
| 13H9C9 + 19C11C10 | 4A7B10 + 5H7C10 | 0 | 1 |
| | 2B9H2 | 0 | 1 |
| | 196 | 0 | 1 |
| 79 | 4A7B10 + 5H7C10 | 0 | 2 |
| | 2B9H2 | 1 | 2 |
| | 196 | 0 | 1 |

Positive assays: number of positive assays
Assay total: total number of assays

Example 11

Detection of the Heterocomplex in the Urine of Patients

The direct detection of the complex in the urine of patients was tested on two representative urines: an MS urine and a normal urine.

The results are described in table 8. These results show that the anti-MRP14 capture antibody/anti-GM2AP detection antibody pairs [4A7B10+5H7C10]/[13D1E5+2G12H5],

[4A7B10+5H7C10]/10E11A11, 2B9H2/[13D1E5+2G12H5] and 2B9H2/[13D9C9+19C11C10] detect the complex.

TABLE 8

| Capture antibody | Detection antibody | Assay number | MS | Normal |
|---|---|---|---|---|
| | | | Urine without proteinase K treatment | |
| 2B9H2 | 13H9C9 + 19C11C10 | 1 | 0 | 0 |
| | | 2 | 0 | 0 |
| 4A7B10 + 5H7C10 | 10E11A11 | 1 | 0.102 | 0.067 |
| | | 2 | 0.030 | 0.011 |
| 4A7B10 + 5H7C10 | 13D1E5 + 2G12H5 | 1 | 0.117 | 0 |
| 2B9H2 | 13D1E5 + 2G12H5 | 1 | 0.152 | 0.006 |
| | | | Urine after proteinase K treatment | |
| 2B9H2 | 13H9C9 + 19C11C10 | 1 | 0.149 | 0.060 |
| | | 2 | 0.141 | 0.020 |
| 4A7B10 + 5H7C10 | 10E11A11 | 1 | 0.130 | 0.087 |
| | | 2 | 0.741 | 0.563 |
| 4A7B10 + 5H7C10 | 13D1E5 + 2G12H5 | 1 | 0.467 | 0.328 |
| 2B9H2 | 13D1E5 + 2G12H5 | 1 | 0.111 | 0.12 |

For the urine treated with proteinase K, there is no concentration with TCA

The methods described in the examples are useful as diagnostic tools for assaying a biological marker for multiple sclerosis, since the correlations between the gliotoxic activity and the clinical situation have proved to be very good[1,3,4].

BIBLIOGRAPHICAL REFERENCES

1. Malcus-Vocanson, C. et al. (1998) A urinary marker for multiple sclerosis [letter]. *Lancet* 351, 1330.
2. Menard, A. et al. (1997) Gliotoxicity, reverse transcriptase activity and retroviral RNA in monocyte/macrophage culture supernatants from patients with multiple sclerosis. *FEBS Lett* 413, 477-85.
3. Menard, A. et al. (1998) Detection of gliotoxic activity in the cerebrospinal fluid from multiple sclerosis patients. *Neurosci Lett* 245, 49-52.
4. Malcus-Vocanson, C. et al. (2001) Glial Toxicity in urine and Multiple Sclerosis. *Multiple Sclerosis* 7, 383-388.
5. N. Benjelloun et al. Cell. Mol. Biol., 1998, 44(4), 579-583.
6. Blazar et al., (1997) Journal of Immunology 159: 5821-5833.
7. Bird et al., (1988) Science 242: 423-426.
8. Arakawa et al., (1996) J. Biochem 120: 657-662.
9. Chaudray et al., (1989) Nature 339: 394-397.
10. Jones et al., Nature 321: 522-525 (1986).
11. Reichmann et al., Nature 332: 323-329 (1988).
12. Presta et al., Curr. Op. Struct. Biol. 2: 593-596 (1992).
13. Galiana et al., J. Neurosci. Res. (1990) 26: 269-277.

The invention claimed is:

1. A method specifically for detecting and/or quantifying a cytotoxic factor having a gliotoxic activity, associated with multiple sclerosis, in a biological sample, comprising:
   isolating a heterocomplex from the biological sample, wherein the heterocomplex is chosen from a GM2AP/GM2/MRP14 heterocomplex and a mutated GM2AP/GM2/MRP14 heterocomplex in which mutated GM2AP has the amino acid sequence set forth in SEQ ID NO:2;
   wherein:
      the heterocomplex is isolated by means of at least one antibody that binds specifically to the heterocomplex, and
      the cytotoxic factor is detected and/or quantified by demonstrating the formation of a complex consisting of the heterocomplex and the antibody.

2. The method as claimed in claim 1, in which the biological sample is selected from the group consisting of serum, plasma, urine and cerebrospinal fluid.

3. The method as claimed in claim 1, according to which the heterocomplex is isolated by means of at least two antibodies that bind specifically to the heterocomplex, and said cytotoxic factor is detected and/or quantified by demonstrating the formation of a complex consisting of the heterocomplex and the two antibodies.

4. The method as claimed in claim 3, according to which the heterocomplex is isolated by means of at least two antibodies, at least one of which binds specifically to GM2AP or mutated GM2AP of the heterocomplex, and at least the other of which binds specifically to MRP14 of the heterocomplex, and said cytotoxic factor is detected and/or quantified by demonstrating the formation of a complex consisting of the heterocomplex and the two antibodies.

5. The method as claimed in claim 4, according to which at least one of said antibodies is a capture antibody and at least one of said antibodies is a detection antibody.

6. The method of claim 1, wherein the biological sample is subjected to the following treatments prior to the step of isolating:
   digesting the proteins of the sample with proteinase K,
   inactivating the proteinase K, and
   neutralizing the pH.

7. The method as claimed in claim 6, wherein inactivating the proteinase K is carried out by precipitation with trichloroacetic acid, and wherein neutralizing the pH is carried out by the addition of a tris-maleate buffer.

8. A method for detecting and/or quantifying a cytotoxic factor having a gliotoxic activity and associated with multiple sclerosis, comprising:
   providing a biological sample,
   digesting the proteins of the sample with proteinase K,
   inactivating the proteinase K,
   neutralizing the pH, and
   isolating a heterocomplex from the biological sample, wherein the heterocomplex is chosen from a GM2AP/GM2/MRP14 heterocomplex and a mutated GM2AP/GM2/MRP14 heterocomplex in which mutated GM2AP has the amino acid sequence set forth in SEQ ID NO:2.

9. The method of claim 8, wherein:
   inactivating the proteinase K is carried out by precipitation with trichloroacetic acid, and
   neutralizing the pH is carried out by the addition of a tris-maleate buffer.

10. The method as claimed in claim 8, wherein the biological sample is selected from the group consisting of serum, plasma, urine, and cerebrospinal fluid.

11. The method of claim 8, wherein:
   the heterocomplex is isolated by means of at least one antibody that binds specifically to the heterocomplex, and the cytotoxic factor is detected and/or quantified by demonstrating the formation of a complex consisting of the heterocomplex and the antibody.

12. The method of claim 8, wherein:
the heterocomplex is isolated by means of at least two antibodies that bind specifically to the heterocomplex, and
the cytotoxic factor is detected and/or quantified by demonstrating the formation of a complex consisting of the heterocomplex and the two antibodies.

13. The method of claim 12, wherein at least one of the antibodies is a capture antibody and at least one antibody is a detection antibody.

14. The method of claim 8, wherein:
the heterocomplex is isolated by means of at least two antibodies, at least one of which binds specifically to GM2AP or mutated GM2AP of the heterocomplex, and at least the other of which binds specifically to MRP14 of the heterocomplex, and
the cytotoxic factor is detected and/or quantified by demonstrating the formation of a complex consisting of the heterocomplex and the two antibodies.

15. A composition for detecting and/or quantifying a cytotoxic factor associated with multiple sclerosis comprising at least one antibody that specifically binds to a heterocomplex selected from the group consisting of:
a GM2AP/GM2/MRP14 heterocomplex and
a mutated GM2AP/GM2/MRP14 heterocomplex in which mutated GM2AP has the amino acid sequence set forth in SEQ ID NO:2.

16. The composition as claimed in claim 15, comprising at least two antibodies that bind specifically to the heterocomplex.

* * * * *

SEQUENCE LISTING

<160> NUMBER OF SEQ ID NOS: 3

<210> SEQ ID NO 1
<211> LENGTH: 193
<212> TYPE: PRT
<213> ORGANISM: Artificial sequence
<220> FEATURE:
<221> NAME/KEY: Site
<222> LOCATION: 153
<223> OTHER INFORMATION: recombinant protein wherein Xaa is Val or Ala
      due to polymorphism

<400> SEQUENCE: 1

Met Gln Ser Leu Met Gln Ala Pro Leu Leu Ile Ala Leu Gly Leu Leu
1               5                   10                  15

Leu Ala Ala Pro Ala Gln Ala His Leu Lys Lys Pro Ser Gln Leu Ser
                20                  25                  30

Ser Phe Ser Trp Asp Asn Cys Asp Glu Gly Lys Asp Pro Ala Val Ile
            35                  40                  45

Arg Ser Leu Thr Leu Glu Pro Asp Pro Ile Ile Val Pro Gly Asn Val
        50                  55                  60

Thr Leu Ser Val Met Gly Ser Thr Ser Val Pro Leu Ser Ser Pro Leu
65                  70                  75                  80

Lys Val Asp Leu Val Leu Glu Lys Glu Val Ala Gly Leu Trp Ile Lys
                85                  90                  95

Ile Pro Cys Thr Asp Tyr Ile Gly Ser Cys Thr Phe Glu His Phe Cys
                100                 105                 110

Asp Val Leu Asp Met Leu Ile Pro Thr Gly Glu Pro Cys Pro Glu Pro
            115                 120                 125

Leu Arg Thr Tyr Gly Leu Pro Cys His Cys Pro Phe Lys Glu Gly Thr
        130                 135                 140

```
Tyr Ser Leu Pro Lys Ser Glu Phe Xaa Val Pro Asp Leu Glu Leu Pro
145                 150                 155                 160

Ser Trp Leu Thr Thr Gly Asn Tyr Arg Ile Lys Ser Val Leu Ser Ser
                165                 170                 175

Ser Gly Lys Arg Leu Gly Cys Ile Lys Ile Ala Ala Ser Leu Lys Gly
            180                 185                 190

Ile

<210> SEQ ID NO 2
<211> LENGTH: 193
<212> TYPE: PRT
<213> ORGANISM: Artificial sequence
<220> FEATURE:
<221> NAME/KEY: Site
<222> LOCATION: 153
<223> OTHER INFORMATION: recombinant protein wherein Xaa is Val or Ala
      due to polymorphism

<400> SEQUENCE: 2

Met Gln Ser Leu Met Gln Ala Pro Leu Leu Ile Ala Leu Gly Leu Leu
1               5                   10                  15

Leu Ala Ala Pro Ala Gln Ala His Leu Lys Lys Pro Ser Gln Leu Ser
                20                  25                  30

Ser Phe Ser Trp Asp Asn Cys Phe Glu Gly Lys Asp Pro Ala Val Ile
        35                  40                  45

Arg Ser Leu Thr Leu Glu Pro Asp Pro Ile Ile Val Pro Gly Asn Val
        50                  55                  60

Thr Leu Ser Val Met Gly Ser Thr Ser Val Pro Leu Ser Ser Pro Leu
65                  70                  75                  80

Lys Val Asp Leu Val Leu Glu Lys Glu Val Ala Gly Leu Trp Ile Lys
                85                  90                  95

Ile Pro Cys Thr Asp Tyr Ile Gly Ser Cys Thr Phe Glu His Phe Cys
            100                 105                 110

Asp Val Leu Asp Met Leu Ile Pro Thr Gly Glu Pro Cys Pro Glu Pro
            115                 120                 125

Leu Arg Thr Tyr Gly Leu Pro Cys His Cys Pro Phe Lys Glu Gly Thr
130                 135                 140

Tyr Ser Leu Pro Lys Ser Glu Phe Xaa Val Pro Asp Leu Glu Leu Pro
145                 150                 155                 160

Ser Trp Leu Thr Thr Gly Asn Tyr Arg Ile Lys Ser Val Leu Ser Ser
                165                 170                 175

Ser Gly Lys Arg Leu Gly Cys Ile Lys Ile Ala Ala Ser Leu Lys Gly
            180                 185                 190

Ile

<210> SEQ ID NO 3
<211> LENGTH: 193
<212> TYPE: PRT
<213> ORGANISM: Artificial sequence
<220> FEATURE:
<223> OTHER INFORMATION: recombinant protein

<400> SEQUENCE: 3

Met Gln Ser Leu Met Gln Ala Pro Leu Leu Ile Ala Leu Gly Leu Leu
1               5                   10                  15

Leu Ala Thr Pro Ala Gln Ala His Leu Lys Lys Pro Ser Gln Leu Ser
                20                  25                  30

Ser Phe Ser Trp Asp Asn Cys Phe Glu Gly Lys Asp Pro Ala Val Ile
```

-continued

```
            35                  40                  45
Arg Ser Leu Thr Leu Glu Pro Asp Pro Ile Val Val Pro Gly Asn Val
     50                  55                  60

Thr Leu Ser Val Val Gly Ser Thr Ser Val Pro Leu Ser Ser Pro Leu
 65              70                  75                  80

Lys Val Asp Leu Val Leu Glu Lys Glu Val Ala Gly Leu Trp Ile Lys
             85                  90                  95

Ile Pro Cys Thr Asp Tyr Ile Gly Ser Cys Thr Phe Glu His Phe Cys
            100                 105                 110

Asp Val Leu Asp Met Leu Ile Pro Thr Gly Glu Pro Cys Pro Glu Pro
            115                 120                 125

Leu Arg Thr Tyr Gly Leu Pro Cys His Cys Pro Phe Lys Glu Gly Thr
        130                 135                 140

Tyr Ser Leu Pro Lys Ser Glu Phe Ala Val Pro Asp Leu Glu Leu Pro
145                 150                 155                 160

Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
            180                 185                 190

Ile
```